(12) United States Patent
Ganesan et al.

(10) Patent No.: US 9,677,121 B2
(45) Date of Patent: Jun. 13, 2017

(54) SYSTEMS AND METHODS FOR THERMAL ACTUATION OF MICROFLUIDIC DEVICES

(71) Applicant: HANDYLAB, INC., Franklin Lakes, NJ (US)

(72) Inventors: Karthik Ganesan, Ann Arbor, MI (US); Kalyan Handique, Ypsilanti, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 66 days.

(21) Appl. No.: 14/550,126

(22) Filed: Nov. 21, 2014

(65) Prior Publication Data
US 2015/0152477 A1 Jun. 4, 2015

Related U.S. Application Data

(60) Continuation of application No. 13/847,415, filed on Mar. 19, 2013, now Pat. No. 8,894,947, which is a
(Continued)

(51) Int. Cl.
*B01L 3/02* (2006.01)
*B01L 3/00* (2006.01)
(Continued)

(52) U.S. Cl.
CPC ........ *C12Q 1/6806* (2013.01); *B01L 3/50273* (2013.01); *B01L 3/502715* (2013.01);
(Continued)

(58) Field of Classification Search
CPC .. B01L 7/52; B01L 3/50273; B01L 3/502738; B01L 7/00; B01L 3/502715; G01N 1/4077
(Continued)

(56) References Cited

U.S. PATENT DOCUMENTS 1,434,314 A   10/1922  Raich
1,616,419 A   2/1927   Wilson
(Continued)

FOREIGN PATENT DOCUMENTS

CA   2294819      1/1999
CN   1968754 A    5/2007
(Continued)

OTHER PUBLICATIONS

Allemand et al., "pH-Dependent Specific Binding and Combing of DNA", Biophys J. (1997) 73(4): 2064-2070.
(Continued)

*Primary Examiner* — Robert A Hopkins
(74) *Attorney, Agent, or Firm* — Knobbe, Martens, Olson & Bear, LLP

(57) ABSTRACT

A microfluidic processing device includes a substrate defining a microfluidic network. The substrate is in thermal communication with a plurality of N independently controllable components and a plurality of input output contacts for connecting the substrate to an external controller. Each component has at least two terminals. Each terminal is in electrical communication with at least one contact. The number of contacts required to independently control the N components is substantially less than the total number of terminals. Upon actuation, the components typically heat a portion of the microfluidic network and/or sense a temperature thereof.

24 Claims, 14 Drawing Sheets

Related U.S. Application Data division of application No. 11/929,877, filed on Oct. 30, 2007, now Pat. No. 8,420,015, which is a continuation of application No. 10/910,255, filed on Aug. 2, 2004, now Pat. No. 7,829,025, which is a continuation-in-part of application No. 10/489,404, filed as application No. PCT/US02/29012 on Sep. 12, 2002, now Pat. No. 7,674,431, application No. 10/910,255, which is a continuation-in-part of application No. 09/949,763, filed on Sep. 12, 2001, now Pat. No. 6,852,287, and a continuation-in-part of application No. 09/819,105, filed on Mar. 28, 2001, now Pat. No. 7,010,391.

(60) Provisional application No. 60/491,264, filed on Jul. 31, 2003, provisional application No. 60/491,539, filed on Aug. 1, 2003, provisional application No. 60/491,269, filed on Jul. 31, 2003, provisional application No. 60/551,785, filed on Mar. 11, 2004, provisional application No. 60/553,553, filed on Mar. 17, 2004.

(51) Int. Cl.
 B01L 7/00 (2006.01)
 G01N 1/40 (2006.01)
 C12Q 1/68 (2006.01)

(52) U.S. Cl.
 CPC ........... B01L 3/502738 (2013.01); B01L 7/00 (2013.01); B01L 7/52 (2013.01); G01N 1/4077 (2013.01); B01L 2200/02 (2013.01); B01L 2200/10 (2013.01); B01L 2200/14 (2013.01); B01L 2200/147 (2013.01); B01L 2300/02 (2013.01); B01L 2300/0681 (2013.01); B01L 2300/087 (2013.01); B01L 2300/0819 (2013.01); B01L 2300/1827 (2013.01); B01L 2400/049 (2013.01); B01L 2400/0442 (2013.01); B01L 2400/0478 (2013.01); B01L 2400/0677 (2013.01)

(58) Field of Classification Search
 USPC ................ 137/561 R; 422/100, 502, 505
 See application file for complete search history.

(56) References Cited

U.S. PATENT DOCUMENTS

| | | |
|---|---|---|
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |

(56) References Cited

U.S. PATENT DOCUMENTS

| | | |
|---|---|---|
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |

(56) References Cited

U.S. PATENT DOCUMENTS

| | | |
|---|---|---|
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |

(56) References Cited

U.S. PATENT DOCUMENTS

| | | |
|---|---|---|
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 * | 6/2003 | Parunak ............ B01L 3/502738 137/251.1 |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-Sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | Dias da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Shinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 * | 5/2006 | Baer .................... B01J 19/0093 219/548 |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | Dias da Silva |
| 7,069,952 B1 | 7/2006 | McReynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |

(56) References Cited

U.S. PATENT DOCUMENTS

| | | |
|---|---|---|
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 | 6/2009 | Sinclair et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| 7,727,371 B2 | 6/2010 | Kennedy et al. |
| 7,727,477 B2 | 6/2010 | Boronkay et al. |
| 7,744,817 B2 | 6/2010 | Bui |
| 7,867,776 B2 | 1/2011 | Kennedy et al. |
| 7,892,819 B2 | 2/2011 | Wilding et al. |
| D637,737 S | 5/2011 | Wilson et al. |
| 7,998,708 B2 | 8/2011 | Handique et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D692,162 S | 10/2013 | Lentz et al. |
| 8,679,831 B2 | 3/2014 | Handique et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| 8,765,076 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0131903 A1 | 9/2002 | Ingenhoven et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0099954 A1 | 5/2003 | Miltenyi et al. |
| 2003/0127327 A1 | 7/2003 | Kurnik |
| 2003/0136679 A1 | 7/2003 | Bohn et al. |
| 2003/0156991 A1 | 8/2003 | Halas et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |

(56) References Cited

U.S. PATENT DOCUMENTS

| | | |
|---|---|---|
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0176230 A1 | 7/2008 | Owen et al. |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2008/0308500 A1 | 12/2008 | Brassard |
| 2009/0047180 A1 | 2/2009 | Kawahara |
| 2009/0047713 A1 | 2/2009 | Handique |
| 2009/0066339 A1 | 3/2009 | Glezer et al. |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0136385 A1 | 5/2009 | Handique et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2010/0009351 A1 | 1/2010 | Brahmasandra et al. |
| 2010/0284864 A1 | 11/2010 | Holenstein et al. |
| 2011/0008825 A1 | 1/2011 | Ingber et al. |
| 2011/0158865 A1 | 6/2011 | Miller et al. |
| 2011/0210257 A9 | 9/2011 | Handique et al. |
| 2011/0300033 A1 | 12/2011 | Battisti |
| 2012/0171759 A1 | 7/2012 | Williams et al. |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan |
| 2013/0183769 A1 | 7/2013 | Tajima |
| 2013/0217013 A1 | 8/2013 | Steel et al. |
| 2013/0251602 A1 | 9/2013 | Handique et al. |
| 2013/0280131 A1 | 10/2013 | Handique et al. |

(56) References Cited

U.S. PATENT DOCUMENTS

| | | |
|---|---|---|
| 2013/0288358 A1 | 10/2013 | Handique et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |
| 2015/0064702 A1 | 3/2015 | Handique et al. |
| 2015/0118684 A1 | 4/2015 | Wu et al. |
| 2015/0133345 A1 | 5/2015 | Handique et al. |
| 2015/0142186 A1 | 5/2015 | Handique et al. |
| 2015/0315631 A1 | 11/2015 | Handique et al. |
| 2015/0328638 A1 | 11/2015 | Handique et al. |
| 2015/0376682 A1 | 12/2015 | Handique |
| 2016/0102305 A1 | 4/2016 | Brahmasandra et al. |
| 2016/0107161 A1 | 4/2016 | Lentz et al. |
| 2016/0250635 A1 | 9/2016 | Handique |
| 2016/0250640 A1 | 9/2016 | Williams et al. |

FOREIGN PATENT DOCUMENTS

| | | |
|---|---|---|
| CN | 103540518 | 1/2014 |
| DE | 19929734 | 12/1999 |
| DE | 19833293 C1 | 1/2000 |
| EP | 0365828 A2 | 5/1990 |
| EP | 0483620 A2 | 5/1992 |
| EP | 0688602 A2 | 12/1995 |
| EP | 0766256 | 4/1997 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-211071 | 8/1996 |
| JP | H08-285859 | 11/1996 |
| JP | H09-325151 | 12/1997 |
| JP | 2001-502790 | 1/1998 |
| JP | H 11-501504 | 2/1999 |
| JP | H 11503315 | 3/1999 |
| JP | 2000-514928 | 4/1999 |
| JP | H 11316226 | 11/1999 |
| JP | H11-515106 | 12/1999 |
| JP | 2000-180455 | 6/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-523812 | 11/2001 |
| JP | 2001-523813 | 11/2001 |
| JP | 2001-527220 | 12/2001 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2004-506179 A | 2/2004 |
| JP | 2004-150797 A | 5/2004 |
| JP | 2004-531360 A | 10/2004 |
| JP | 2004-533838 | 11/2004 |
| JP | 2004-361421 | 12/2004 |
| JP | 2004-536291 | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-176613 A | 7/2005 |
| JP | 2005-192439 | 7/2005 |
| JP | 2005-192554 | 7/2005 |
| JP | 2005-204661 | 8/2005 |
| JP | 2005-525816 | 9/2005 |
| JP | 2005-291954 A | 10/2005 |
| JP | 2005-323519 | 11/2005 |
| JP | 2006-021156 A | 1/2006 |
| JP | 2006-094866 A | 4/2006 |
| JP | 2006-145458 | 6/2006 |
| JP | 2006-167569 | 6/2006 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2005-542207 | 12/2009 |
| JP | 2009-542207 | 12/2009 |
| WO | WO 88/06633 | 9/1988 |
| WO | WO 94/11103 | 5/1994 |
| WO | WO 96/04547 | 2/1996 |
| WO | WO 97/21090 | 6/1997 |
| WO | WO 98/35013 A1 | 8/1998 |
| WO | WO 98/49548 | 11/1998 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/007677 | 1/2003 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 03/087410 | 10/2003 |
| WO | WO 2004/007081 | 1/2004 |
| WO | WO 2004/048545 | 6/2004 |
| WO | WO 2004/055522 | 7/2004 |
| WO | WO 2004/056485 A1 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |

(56) References Cited

FOREIGN PATENT DOCUMENTS

| WO | WO 2006/079082 | 7/2006 |
|---|---|---|
| WO | WO 2006/081995 | 8/2006 |
| WO | WO 2006/113198 | 10/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/030914 | 3/2008 |
| WO | WO 2009/012185 | 1/2009 |
| WO | WO 2009/054870 A2 | 4/2009 |
| WO | WO 2010/118541 | 10/2010 |
| WO | WO 2010/140680 | 12/2010 |
| WO | WO 2011/101467 | 8/2011 |

OTHER PUBLICATIONS

Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-spermine-sepharose", Nucl Acids Res. (1989) 17(17): 6947-6958.
Labchem; Sodium Hydroxide, 0,5N (0.5M); Safety Data Sheet, 2015; 8 pages.
Sarma, K.S., "Liquid Crystal Displays", Chapter 32 in Electrical Measurement, Signal Processing, Displays, Jul. 15, 2003, ISBN: 978-0-8493-1733-0, Retrieved from the Internet: URL: http://http://197.14.51.10:81/pmb/ELECTRONIQUE/Electrical Measurement Signal Processing and Displays/Book/1733ch32.pdf; 21 pages.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems, SPIE Conference on Microfluidic Devices and Systems, 1998, vol. 3515, pp. 242-251, Santa Clara, CA.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Burns et al., "An Integrated Nanoliter DNA Analysis Device", Science 282:484-487 (1998).
Carlen et al., "Paraffin Actuated Surface Micromachined Valve," in IEEE MEMS 2000 Conference, Miyazaki, Japan, (Jan. 2000) pp. 381-385.
Chung, Y. et al., "Microfluidic chip for high efficiency DNA extraction", Miniaturisation for Chemistry, Biology & Bioengineering, vol. 4, No. 2 (Apr. 2004), pp. 141-147.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Handique et al, "Microfluidic flow control using selective hydrophobic patterning", SPIE, (1997) 3224: 185-194.
Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique, K. et al., "Nanoliter Liquid Metering in Microchannels Using Hydrophibic Patterns", Anal Chem., 72:4100-4109 (2000).
Handique, K. et al., "Mathematical Modeling of Drop Mixing in a Slit-Type Microchannel", J. Micromech. Microeng., 11:548-554 (2001).
Handique et al., On-Chip Thermopneumatic Pressure for Discrete Drop Pumping, Analytical Chemistry, American Chemical Society, Apr. 15, 2001, vol. 73, No. 8, 1831-1838.

He, et al., Microfabricated Filters for Microfluidic Analytical Systems, Analytical Chemistry, American Chemical Society, 1999, vol. 71, No. 7, pp. 1464-1468.
Ibrahim, et al., Real-Time Microchip PCR for Detecting Single-Base Differences in Viral and Human DNA, Analytical Chemistry, American Chemical Society, 1998, 70(9): 2013-2017.
Khandurina et al., Microfabricated Porous Membrane Structure for Sample Concentration and Electrophoretic Analysis, Analytical Chemistry American Chemical Society, 1999, 71(9): 1815-1819.
Kopp et al., Chemical Amplification: Continuous-Flow PCR on a Chip, www.sciencemag.org, 1998, vol. 280, pp. 1046-1048.
Kutter et al., Solid Phase Extraction on Microfluidic Devices, J. Microcolumn Separations, John Wiley & Sons, Inc., 2000, 12(2): 93-97.
Lagally et al., Single-Molecule DNA Amplification and Analysis in an Integrated Microfluidic Device, Analytical Chemistry, American Chemical Society, 2001, 73(3): 565-570.
Livache et al., "Polypyrrole DNA chip on a Silicon Device: Example of Hepatitis C Virus Genotyping", Analytical Biochemistry, (1998) 255: 188-194.
Mascini et al., "DNA electrochemical biosensors", Fresenius J. Anal. Chem., 369: 15-22, (2001).
Meyers, R.A., Molecular Biology and Biotechnology: A Comprehensive Desk Reference; VCH Publishers, Inc. New York, NY; (1995) pp. 418-419.
Nakagawa et al., Fabrication of amino silane-coated microchip for DNA extraction from whole blood, J of Biotechnology, Mar. 2, 2005, vol. 116, pp. 105-111.
Northrup et al., A Miniature Analytical Instrument for Nucleic Acids Based on Micromachined Silicon Reaction Chambers, Analytical Chemistry, American Chemical Society, 1998, 70(5): 918-922.
Oleschuk et al., Trapping of Bead-Based Reagents within Microfluidic Systems,: On-Chip Solid-Phase Extraction and Electrochromatography, Analytical Chemistry, American Chemical Society, 2000, 72(3): 585-590.
Plambeck et al., "Electrochemical Studies of Antitumor Antibiotics", J. Electrochem Soc.: Electrochemical Science and Technology (1984), 131(11): 2556-2563.
Roche, et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Shoffner et al., Chip PCR.I. Surface Passivation of Microfabricated Silicon-Glass Chips for PCR, Nucleic Acids Research, Oxford University Press, (1996) 24(2): 375-379.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Wang, "Survey and Summary, from DNA Biosensors to Gene Chips", Nucleic Acids Research, 28(16):3011-3016, (2000).
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Yoza et al., "Fully Automated DNA Extraction from Blood Using Magnetic Particles Modified with a Hyperbranched Polyamidomine Dendrimer", Journal of Bioscience and Bioengineering, 2003, 95(1): 21-26.
Yoza et al., DNA extraction using bacterial magnetic particles modified with hyperbranched polyamidoamine dendrimer, Mar. 20, 2003, 101(3): 219-228.
International Search Report dated Feb. 28, 2003 for Application No. PCT/US2002/029012, filed Sep. 12, 2002.
International Preliminary Examination Report dated Mar. 12, 2004 for Application No. PCT/US2002/029012, filed Sep. 12, 2002.
Supplemental European Search Report dated Jun. 4, 2010 for Application No. 02761632.5, filed Sep. 12, 2002.

(56) References Cited

OTHER PUBLICATIONS

Kuo et al., "Remnant cationic dendrimres block RNA migration in electrophoresis after monophasic lysis", J Biotech. (2007) 129: 383-390.
Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.
Wu et al., "Polycationic dendrimers interact with RNA molecules: polyamine dendrimers inhibit the catalytic activity of Candida ribozymes", Chem Commun. (2005) 3: 313-315.
Zhou et al., "Cooperative binding and self-assembling behavior of cationic low molecular-weight dendrons with RNA molecules", Org Biomol Chem. (2006) 4(3): 581-585.
Zhou et al., "PANAM dendrimers for efficient siRNA delivery and potent gene silencing", Chem Comm.(Camb.) (2006) 22: 2362-2364.
Broyles et al., "Sample Filtration, Concentration, and Separation Integrated on Microfluidic Devices" Analytical Chemistry (American Chemical Society), (2003) 75(11): 2761-2767.

\* cited by examiner

SYSTEMS AND METHODS FOR THERMAL ACTUATION OF MICROFLUIDIC DEVICES

RELATED APPLICATIONS

This application is a continuation of U.S. application Ser. No. 13/847,415, filed Mar. 19, 2013 and scheduled to issue on Nov. 25, 2014 as U.S. Pat. No. 8,894,947, which is a divisional of U.S. application Ser. No. 11/929,877, filed Oct. 30, 2007 and issued as U.S. Pat. No. 8,420,015 on Apr. 16, 2013, which is a continuation of U.S. application Ser. No. 10/910,255, filed Aug. 2, 2004 and issued as U.S. Pat. No. 7,829,025 on Nov. 9, 2010, which is a continuation-in-part of (a) U.S. application Ser. No. 10/489,404, with a §371(c) date of Mar. 7, 2005 and issued as U.S. Pat. No. 7,674,431 on Mar. 9, 2010, which is a U.S. national stage application of International Application No. PCT/US02/29012, filed Sep. 12, 2002; (b) U.S. application Ser. No. 09/949,763, filed Sep. 12, 2001 and issued as U.S. Pat. No. 6,852,287 on Feb. 8, 2005; and (c) U.S. application Ser. No. 09/819,105, filed Mar. 28, 2001 and issued as U.S. Pat. No. 7,010,391 on Mar. 7, 2006. U.S. application Ser. No. 10/910,255 also claims the benefit of U.S. Provisional Application No. 60/491,264, filed Jul. 31, 2003; U.S. Provisional Application No. 60/491,539, filed Aug. 1, 2003; U.S. Provisional Application No. 60/491,269, filed Jul. 31, 2003, U.S. Provisional Application No. 60/551,785, filed Mar. 11, 2004; and U.S. Provisional Application No. 60/553,553, filed Mar. 17, 2004. The disclosures of all of the above-referenced prior applications, publications, and patents are considered part of the disclosure of this application, and are incorporated by reference herein in their entirety.

FIELD OF THE INVENTION

The present invention relates to microfluidic devices, and more particularly to systems and methods for operating microfluidic devices.

BACKGROUND

Microfluidic devices are typically configured to manipulate minute amounts of materials, such as to determine the presence and/or amount of a target compound within a sample. The devices manipulate materials within a microfluidic network, which generally includes elements such as valves, gates, pumps, reaction chambers, mixing chambers, enrichment modules, filtration modules, and detection modules. These elements can be thermally actuated under computer control.

SUMMARY

One aspect of the invention relates to a microfluidic device for processing microfluidic samples. The processing device can include thermally actuated elements, such as one or more of a valve, a pump, or a reaction chamber, configured to manipulate materials, e.g., microfluidic samples and/or reagents, within the device. The device, or a system configured to operate the device, can also include a plurality N of independently controllable components, each component having at least two terminals, at least one of the components configured to actuate the at least one element of the device. For example, a component may be configured to actuate a valve and a component may be configured to actuate a pump of the device. In general the components are heat sources or temperature sensors. In some embodiments, at least some of the components are both heat sources and temperature sensors.

The device typically includes a plurality of input/output contacts for electrically connecting the components to a controller, wherein the number of contacts required to independently control the N components is substantially less than the total number of terminals.

In some embodiments, each contact is electrically connected to at least one terminal of each of at least two of the N components, and wherein the terminals of the N components are connected to a unique combination of the contacts, so that the external controller can control each component independently of other components.

The device can include a plurality of current flow directional elements, e.g., diodes. Each current flow directional element can be configured to allow current to flow in essentially only one direction through at least one of the components. An electrical pathway between each contact and at least one terminal of each component can include a current flow directional element. Each component can include a corresponding current flow directional element.

In some embodiments, at least one of the components includes a plurality of active regions each active region disposed in thermal contact with a respective thermally actuated element of the microfluidic device. Upon the passage of current through the at least one component, each of the active regions generates an amount of heat sufficient to actuate the respective element of the microfluidic device. The active regions are spaced apart by regions that do not generate sufficient heat to actuate a thermally actuated element of the microfluidic device.

In some embodiments, at least one of the components has a temperature sensitive resistance. The system can include a processor configured to actuate first and second actuation states of the component. In the first action state of the component, the component generates an amount of heat sufficient to actuate an element of the microfluidic network. In a second actuation state, a temperature dependent electrical characteristic of the component is determined. The temperature dependent electrical characteristic is indicative of a temperature of the component and, typically, of a portion of the corresponding element of the microfluidic element or material therein. The first and second actuation states of the component can be repeated.

In some embodiments, a method for fabricating a microfluidic processing device includes providing a substrate having a plurality of components each having at least two terminals and providing a plurality of input/output contacts for connecting the substrate to an external controller. A plurality of leads are provided for connecting the contacts to the terminals. The number of contacts required to independently control the N components is substantially less than the total number of terminals, and wherein the controller can thereby control each the component independently of each other component.

The method can include providing a plurality of current flow directional elements configured to allow current to flow in essentially only one direction through each of at least some of the N components. The current flow directional elements are typically diodes.

In some embodiments, a microfluidic system includes a substrate including a microfluidic network including at least one of each of a thermally actuated valve, a thermally actuated pump, and a thermally actuated reaction chamber. The system also includes a plurality of components and a plurality of electrical contacts. Each component is in thermal communication with a respective one of the valve, pump, and reaction chamber. Each contact is in electrical communication with at least two different components. Each component is in electrical communication with at least a pair of contacts. No component of at least a subset of the components is in electrical communication with the same pair of contacts.

Another aspect of the invention relates to a system for operating a microfluidic device. The system typically includes a microfluidic device comprising a channel configured to receive a fluidic sample, an electrical pathway comprising a resistive element disposed in thermal communication with the channel, the resistive element having a temperature-dependent resistance, an electrical energy source in electrical communication with the electrical pathway, and an electrical measurement device configured to obtain data indicative of an electrical characteristic of the resistive element.

The system includes a computer-readable medium comprising: code to provide a first actuation state of the electrical energy source, wherein a first electrical current flows through the resistive element, code to provide a second actuation state of the electrical energy source. A second, lower electrical current flows through the resistive element during the second actuation state. The computer-readable medium also includes code to receive data indicative of the electrical characteristic of the resistive element from the electrical measurement device.

In some embodiments, the computer-readable medium of claim comprises code to determine a temperature of the resistive element based on the data indicative of the electrical characteristic of the resistive element received from the electrical measurement device. The data indicative of the electrical characteristic of the resistive element can be indicative of a temperature-dependent resistance of the resistive element. The code can be configured such that the data indicative of the temperature-dependent resistance of the resistive element is obtained while the electrical energy source is in the second actuation state.

The data indicative of the electrical characteristic of the resistive element may be indicative of an electrical potential required to cause a predetermined current to flow through the resistive element while the electrical energy source is in the second actuation state.

The computer-readable medium may include code to determine a temperature of the resistive element based on the data indicative of the electrical characteristic of the resistive element received from the electrical measurement device. The data may be indicative of the electrical characteristic of the resistive element when the electrical energy source is in the second actuation state. Also included is code to compare the temperature of the resistive element with a predetermined temperature value and code to repeat the first and second actuation states of the electrical energy source if the temperature is less than the predetermined temperature value.

The computer-readable medium may include code to compare, based upon the received data indicative of the electrical characteristic: the second, lower current and a predetermined current, and code to increase an electrical potential across the resistive element during the second actuation state if the second, lower current is less than the predetermined current, code to decrease an electrical potential across the resistive element during the second actuation state if the second, lower current exceeds the predetermined current, and code to receive electrical potential data indicative of the electrical potential across the resistive element during the second actuation state if the second, lower current is within a predetermined range of the predetermined current.

The computer-readable medium can include code to determine the temperature of the resistive element based on the electrical potential across the resistive element when the second, lower current is within the predetermined range of the predetermined current.

The computer-readable medium can include code to provide the first actuation state of the electrical energy source if the temperature of the resistive element is less than a predetermined temperature. The computer-readable medium can include code to repeatedly determine the temperature of the resistive element based on the electrical potential across the resistive element when the second, lower current is within the predetermined range of the predetermined current and provide the first actuation state of the electrical energy source if the temperature of the resistive element is less than the predetermined temperature.

In some embodiments, the resistive element has a thermal dissipation constant (DC) and, during the first actuation state, the code can be configured to control the resistive element to dissipate a power k, wherein the ratio k/DC ≥40° C., ≥55° C., or ≥65° C. The ratio may be k/DC<300° C., <250° C., <200° C., <175° C., or <150° C.

Another aspect of the invention relates to a method for monitoring a temperature of material present within a channel of a microfluidic device. The method can include providing a microfluidic device including a channel and an electrical pathway comprising a resistive element in thermal communication with the channel. A liquid sample is introduced into the channel. A first electrical current is caused to flow through the electrical pathway by applying a first electrical potential across the resistive element. A second, predefined and lower, electrical current is caused to flow through the electrical pathway by applying a second electrical potential across the resistive element. A temperature of the fluidic material is determined based upon the second electrical potential required to cause the second electrical current to flow through the electrical circuit.

The resistive element can be a platinum-comprising conductor having a temperature-dependent resistance.

In some embodiments, a method for operating a microfluidic system to monitor a temperature of material present within a channel of a microfluidic device includes providing a microfluidic analysis system including a microfluidic device. The microfluidic device includes a microfluidic network comprising at least one channel. The system includes an electrical pathway comprising a junction between a first material and a second, different material, at least a portion of one of the first and second materials are in thermal communication with the channel. Application of an electrical current across the junction increases a temperature of the at least a portion of one of the first and second materials. The junction comprises at least one temperature-dependent electrical characteristic. The system also includes a source of electrical current.

A liquid sample is introduced into the channel. A first electrical current is applied across the junction. The first electrical current is generated by the source of electrical current and is sufficient to heat the at least a portion of one of the first and second materials to at least 30° C. Data indicative of the at least one temperature-dependent electrical characteristic of the junction are obtained. A temperature of the liquid sample is determined based upon the data.

The step of obtaining data indicative of the at least one temperature-dependent electrical characteristic can be performed after performing the step of applying a first electrical current. Prior to the step of obtaining data, the method can include reducing the first electrical current to an amount insufficient to heat the at least one portion of one of the first and second materials to at least 30° C.

In some embodiments a method for monitoring a temperature of material present within a channel of a microfluidic device of a microfluidic system includes introducing a liquid sample to the channel, applying a first electrical potential to an electrical pathway in thermal communication with the channel, applying a second, lower, electrical potential to the electrical pathway, and determining a temperature of the fluidic material based upon a current that flows through the electrical pathway when the second potential is applied.

Another aspect of the invention relates to a method for monitoring a temperature of a thermally actuated valve. The method includes providing a microfluidic system including a microfluidic device. The device includes a channel having an upstream portion and a downstream portion and a valve comprising a closed state and an open state. Upon changing a temperature of at least a first portion of the valve, the valve transitions from one of the closed or open states to the other state. The system also includes an electrical pathway comprising a resistive element in thermal communication with the first portion of the valve. A first electrical potential is applied to the circuit. A second, lower, potential is applied to the electrical pathway. A temperature of the first portion of the valve is determined based upon a current that flows through the electrical circuit when the second potential is applied.

Another aspect of the invention relates to a method of calibrating a resistive heating element of a microfluidic device. The method can include manufacturing a first microfluidic device. The first device includes a microfluidic network including a channel configured to receive a liquid sample therein. The channel is located in thermal contact with a resistive element of an electrical pathway. A liquid sample is introduced to the channel. The liquid sample includes at least one component exhibiting a temperature dependent physio-chemical property at a known temperature. An amount of electrical current required to heat the liquid sample to a temperature sufficient to observe the physio-chemical property of the fluidic sample is determined.

A second microfabricated device can be manufactured. The second device includes a channel configured to receive a fluidic sample therein and is configured to be operated in thermal communication with a resistive element of an electrical pathway. The amount of electrical current required to heat a liquid sample present in the channel of the second device to a predetermined temperature is determined based on the amount of current required to heat the liquid sample is the first device.

Typically, the devices include an injection-molded substrate. The temperature is typically between 60° C. and 90° C. The physio-chemical property can be the enzyme-based amplification of a polynucleotide. The physio-chemical property may be a phase transition of a temperature response material, e.g., wax.

A computer-readable medium can be provided with current to operate an electrical energy source to cause an amount of current to flow the resistive element of the second microfluidic device.

Another aspect of the invention relates to a method for calibrating a heat source of a microfluidic system. The method includes manufacturing a first microfluidic device defining a microfluidic network including a channel configured to receive a fluidic sample therein. The device is operated using a microfluidic system including an electrical pathway comprising an electrical element in thermal communication with the channel. A liquid sample is introduced to the channel. The liquid sample includes at least one component exhibiting a temperature dependent physio-chemical property at a known temperature. An amount of electrical energy required to heat the fluidic sample to a temperature sufficient to observe the physio-chemical property of the fluidic sample is determined.

The method can also include manufacturing a second microfluidic device defining a microfluidic network including a channel configured to receive a liquid sample therein. Instructing a user to operate the microfluidic device with the channel in thermal contact with a heat source. Instructing the user to introduce a fluidic sample to the channel and providing a computer-readable medium including code configured to actuate the heat source to heat the liquid sample in the channel. The code is configured to actuate an electrical energy source to provide an amount of electrical energy determined on the basis of the amount of electrical energy required. to heat the fluidic sample present in the first microfluidic device to a temperature sufficient to observe the physio-chemical property of the fluidic sample.

Another aspect of the invention relates to a microfluidic system including a microfluidic device defining a microfluidic network including at least one thermopneumatic pressure source. The system also includes at least two thermopneumatically actuated components in gaseous communication with the thermopneumatic pressure source, wherein, pressure within the thermopneumatic pressure source simultaneously actuates each of two thermopneumatically actuated components.

In some embodiments, each of the thermopneumatically actuated components includes a respective mass of thermally responsive substance (TRS). The masses of TRS are spaced apart from one another. The pressure from the pressure source simultaneously moves each of the masses of TRS. The components may be valves or gates configured to obstruct or allow passage of sample and/or reagents along a channel. Upon actuation, one or more of the masses of TRS may pass along the channel in a direction of flow of the sample and/or reagents.

In some embodiments, neither of the at least two thermopneumatically actuated components can be actuated independently of the other of the at least two thermopneumatically actuated components.

Another aspect of the invention relates to a microfluidic system. The system includes a microfluidic device defining a microfluidic network including first and second thermally actuated components. The system also includes first and second resistive heat sources in series with and spaced apart by a first more conductive region. The first thermally actuated component is in thermal communication with the first heat source and the second thermally actuated component is in thermal communication with the second heat source.

Upon the passage of a current through the first heat source, the first more conductive region, and the second heat source, the first heat source generates an amount of heat sufficient to actuate the first thermally actuated component but insufficient to actuate the second thermally actuated component and the second heat source generates an amount of heat sufficient to actuate the second thermally actuated component but insufficient to actuate the first thermally actuated component. The first more conductive region generates an amount of heat insufficient to actuate either of the first and second thermally actuated components.

Other features and advantages of the invention are apparent from the following description, and from the claims.

DETAILED DESCRIPTION

Microfluidic devices generally include a substrate that defines one or more microfluidic networks, each including one or more channels, process modules, and actuators. Materials, e.g., samples and reagents, are manipulated within the microfluidic network(s), generally to determine the presence or absence of some target.

Modules and actuators of typical networks are thermally actuated. For example, a process module can include a reaction chamber or lysing chamber that is heated by a heat source. An actuator may include a chamber that is heated to generate a pressure or a vacuum to move material within the network.

Aspects of the present invention relate to thermal actuation of components of microfluidic networks. Before undertaking a detailed discussion, however, exemplary microfluidic devices, systems and typically analyzed samples are introduced.

Microfluidic Systems, Devices And Samples

Figure 1:
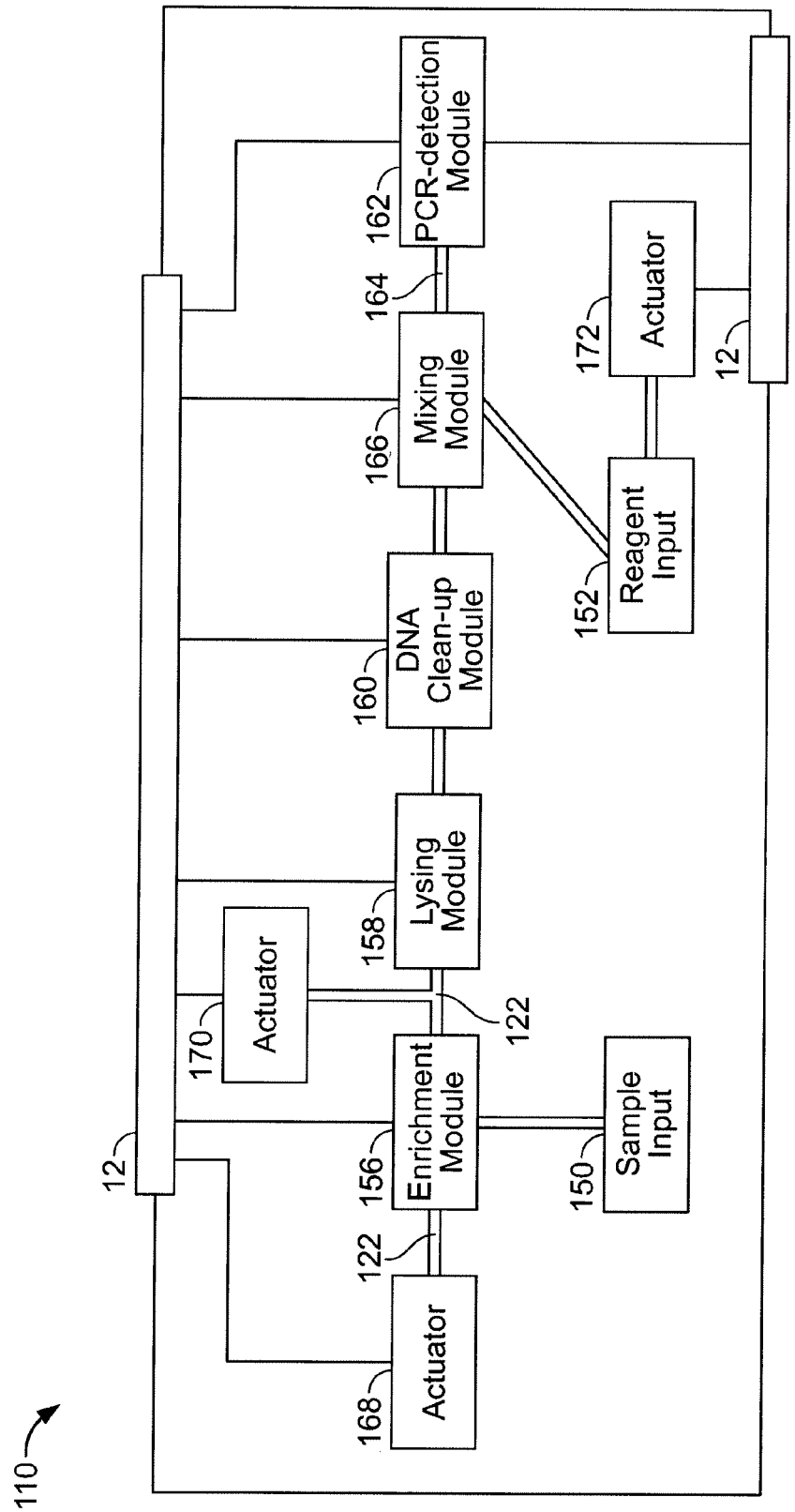
FIG. 1 is a schematic of an exemplary microfluidic device.

Referring to FIG. 1, an exemplary microfluidic network 110 of a microfluidic device has a sample input module 150 and reagent input module 152 to allow sample and reagent materials, respectively, to be input to device 110. Generally, one or both of input modules 150, 152 are configured to allow automatic material input using a computer controlled laboratory robot Network 110 may also include output ports configured to allow withdrawal or output of processed sample from or by microfluidic network 110.

Typical samples include particle-containing fluidic samples. The fluid component of the particle-containing fluidic sample may include a gas and/or, a liquid, e.g., a buffer, water, organic solvents, saliva, urine, serum, blood, or combination thereof. In any case, the fluid typically entrains the particles such that the particles tend to move with the fluid.

The particles of the particle-containing fluidic sample generally include cells, such as bacterial cells or cells of an animal, such as a human. The particles may include intracellular material released from such cells. For example, the microfluidic systems may detect (upon optional amplification) polynucleotides, e.g., DNA, released from cells. In some embodiments, the microfluidic system processes DNA released from bacteria cells to determine the presence, absence, and/or abundance of the bacteria, e.g., bacteria associated with Group B streptococcal (GBS) disease. Other particles that may be analyzed include tissue, viruses, spores, fungi, and other microorganisms and material released from within such particles.

Within a microfluidic network, sample and reagent materials generally travel from upstream locations to downstream locations. For example, sample material generally travels downstream from an input port to other locations within the microfluidic network. In some cases, however, the direction of flow may be reversed.

Locations of network 110 downstream from the input module typically include process modules 156, 158, 160, 166 and 162 for processing the sample and reagent materials. Within these process modules, a sample is subjected to various physical and chemical process steps. For example, enrichment module 156 receives a particle-containing fluid and prepares a fluid sample having a relatively higher concentration of particles. Lysing module 158 releases material from particles of an enriched sample, e.g., the module can release intracellular material from cells. Lysing can be accomplished using, for example, thermal, ultrasonic, mechanical, or electrical techniques. Exemplary lysing and enrichment modules are discussed in U.S. provisional application No. 60/491,269, filed Jul. 31, 2003, International application no. PCT/US2004/025181 filed concurrently herewith and titled Processing Particle-Containing Samples (The Processing Application), and U.S. patent application Ser. No. 10/014,519, filed Dec. 14, 2001, which applications are incorporated herein by reference.

DNA clean-up module 160 readies polynucleotides, e.g., DNA, released from the particles for detection. For example, DNA clean-up module 160 can be configured to prepare a DNA sample for amplification by polymerase chain reaction. Sample DNA processed by clean-up module 160 moves downstream within network 110. An exemplary DNA clean-up module is discussed in U.S. provisional application No. 60/567,174, filed May 3, 2004, which application is incorporated herein by reference.

Mixing module 166 mixes DNA received from module 160 with reagents from reagent input module 152. Typical reagents include PCR primers, reagents, and controls.

Exemplary reagents are used in the amplification and detection of bacteria, e.g., GBS bacteria. Such reagents are disclosed in U.S. patent application Ser. No. 10/102,513, filed Mar. 20, 2002, which application is incorporated herein. Reagent materials may be loaded during use and/or stored within the microfluidic device during manufacturing. Certain reagent materials can be lyophilized to extend their storage life. Liquid reagents can be stored within a chamber, e.g., a metalized pouch, for mixing with dried reagents.

Amplification process module 162 receives DNA released from sample particles and reagents and detects minute quantities of DNA therein. In general, process module 162 is configured to amplify the DNA such as by PCR. Detection is typically spectroscopic, as by fluorescence. In some embodiments, the presence and/or abundance of DNA is detected electrochemically.

Detection module 162 typically includes more than one amplification/detection chamber. One chamber generally receives and detects (with optional amplification) DNA released from sample particles. Another chamber typically receives and detects (with optional amplification) control DNA, which may be used to indicate whether network 110 is functioning properly. Other modules of network 110, e.g., reagent and mixing modules 152,166 are configured to accommodate the presence of more than one amplification/detection chamber.

Various modules of microfluidic network 110 are connected, such as by channels 164, to allow materials to be moved from one location to another within the network 110. Actuators 168, 170, 172 associated with the microfluidic device provide a motive force, such as an increased gas pressure and/or a decreased gas pressure to move the sample and reagent material along the channels and between modules. Some gas actuators move materials by reducing a pressure in a downstream portion of a microfluidic network relative to a pressure in an upstream portion of the microfluidic network. The resulting pressure differential moves the material downstream toward the region of reduced pressure. Fluid control elements, e.g., valves, gates, vents, and hydrophobic patches, allow additional control over movement and/or positioning of the materials.

As used herein, the term vacuum does not require the total absence of gas or other material. Rather, a vacuum means a region having at least a reduced gas pressure as compared to another region of the microfluidic device, e.g., a partial vacuum. The volume of channels and chambers associated with a vacuum actuator is typically reduced by placing fluid control elements, e.g., valves or gates, as near to the vacuum chamber of the actuator as is feasible.

First actuator 168 of network 110 moves material downstream from enrichment module 156 to lysing module 158. Upon completion of processing within lysing module 158, a second actuator 170 moves material downstream to DNA clean-up module 160. Subsequently, actuator 170 or an additional actuator moves cleaned-up DNA to mixing module 166, where the material mixes with a reagent moved by actuator 172. Finally, actuator 172, or another actuator, moves the mixed material to detection module 162.

Material moved or otherwise manipulated and processed by the microfluidic device can be in the form of a microdroplet having upstream and downstream termini typically defined by a liquid gas interface. In some embodiments, the microdroplets have a volume of 25 µl or less, 10 µl or less, 2.5 µl or less, 1 µl or less, 0.5 µl or less, or 0.3 µl or less. Various features of the microfluidic device can be sized to accommodate such microdroplets. For example, channels and chambers can have a width of less than 200 µm and a depth of Jess than 50 µm. In general, the microdroplets have a length that is substantially shorter than a length of the channels through which the microdroplets move.

As used herein, the term microfluidic system includes not only a microfluidic device defining a microfluidic network but also the heat sources to operate thermally actuated modules, fluid control elements, and actuators of the microfluidic device. The heat sources can be integrated with the microfluidic device or incorporated in another component of the microfluidic system such as a receptacle that receives the microfluidic device during operation. The various functional elements, of microfluidic network 110, including the heat sources, are typically under computer control to allow automatic sample processing and analysis. Systems and methods for computer control of microfluidic systems are disclosed in U.S. patent application Ser. No. 09/819,105, filed Mar. 28, 2001, which application is incorporated herein by reference.

Control of Microfluidic Systems and Devices

Figure 2:
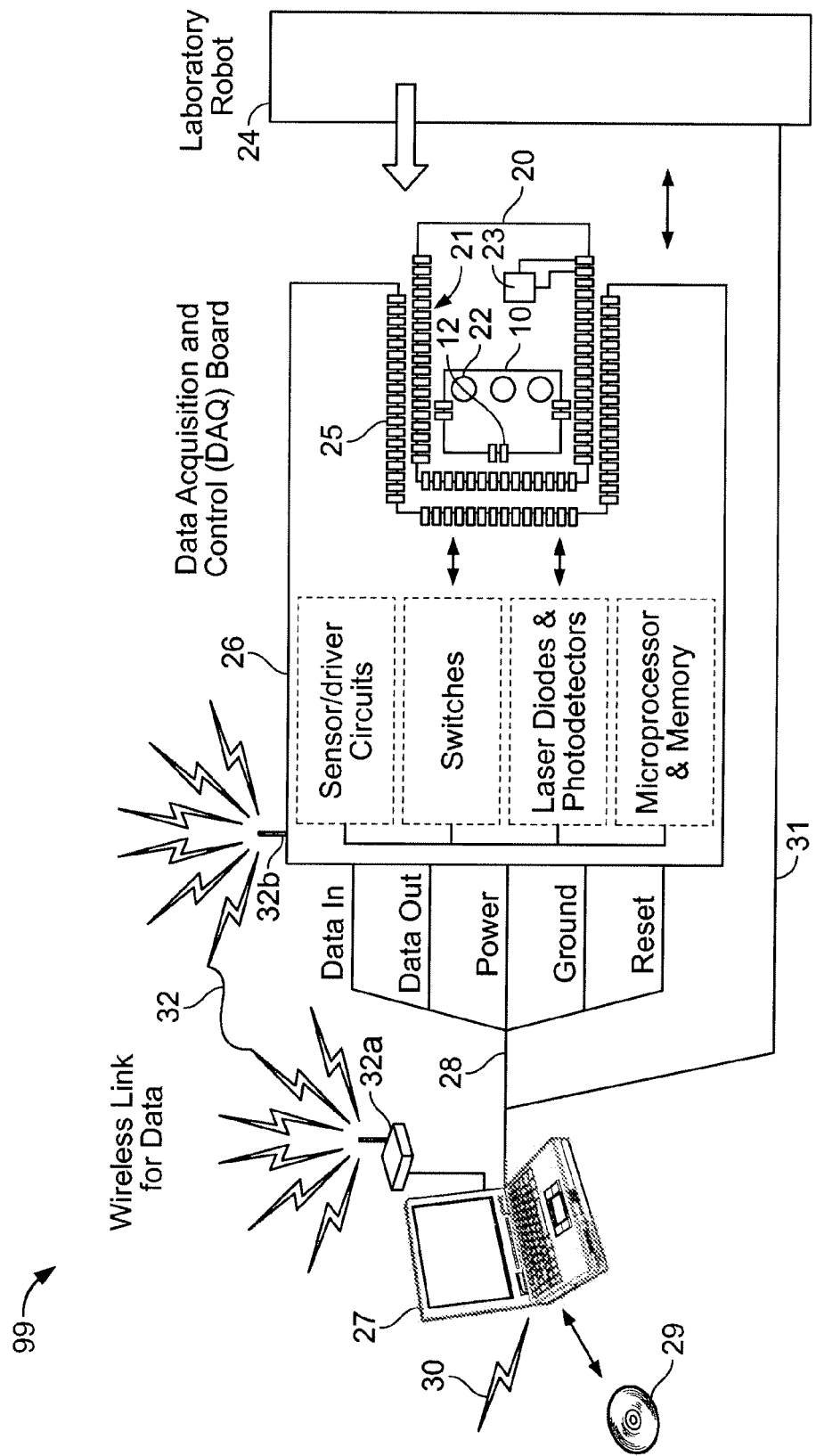
FIG. 2 is a microfluidic control system having a discrete droplet microfluidic processing device, an external controller, and a general purpose computer.

Referring to FIG. 2, an exemplary microfluidic system 99 includes a microfluidic device 10, a chip carrier cartridge 20, a data acquisition and control board ("DAQ") 26, and a processor 27 such as a laptop or palmtop computer.

Figure 3:
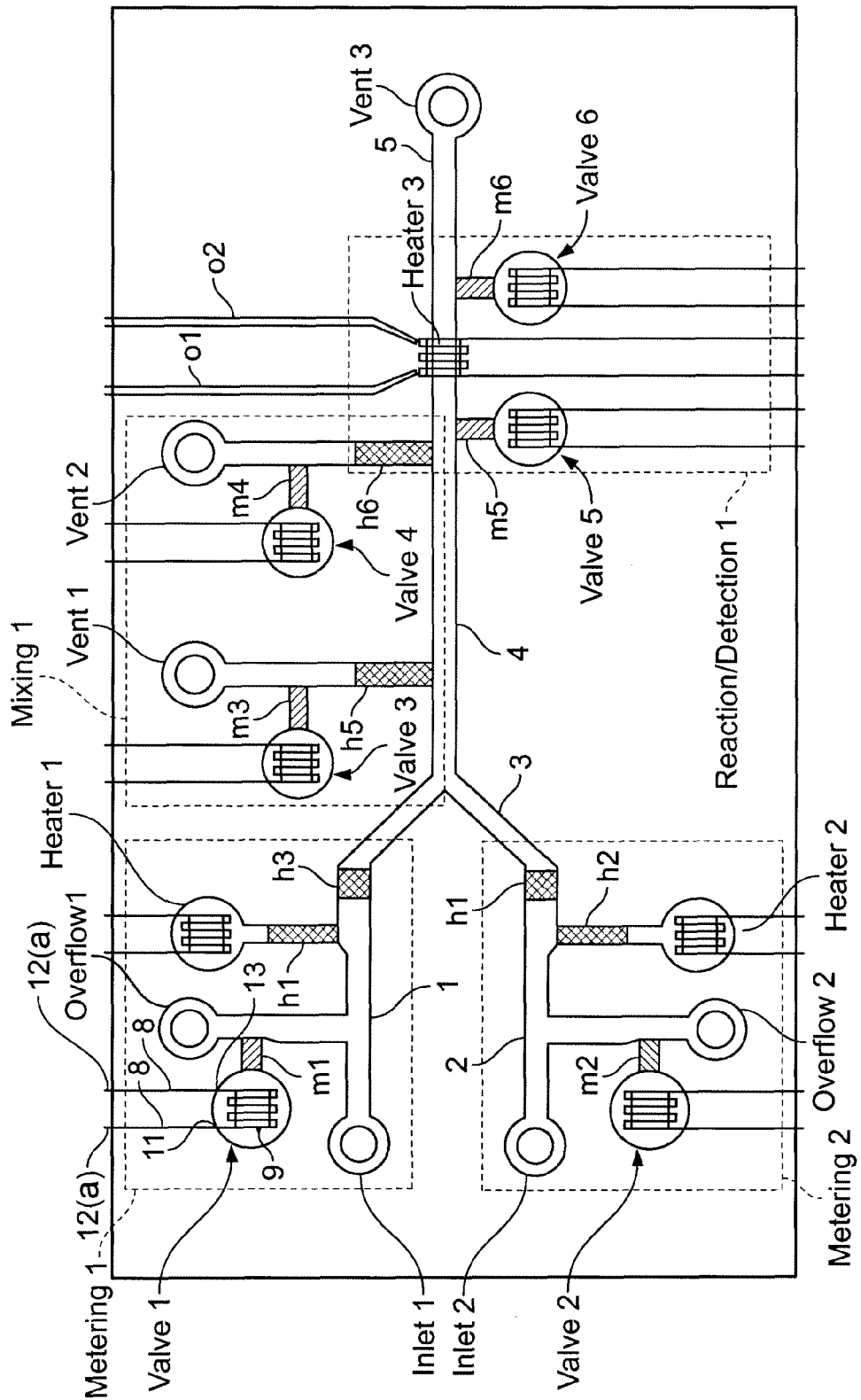
FIG. 3 illustrates the discrete droplet microfluidic processing device of FIG. 2.

Referring also to FIG. 3, microfluidic device 10 has a microfluidic network including microchannels and elements, e.g., valves, pumps, reaction modules, detection modules, and the like, defined using one or more substrates, which can include, e.g., silicon, glass, polymer, or other suitable material. The microfluidic network can be fabricated using photolithography, injection molding, impression molding and other techniques. Injection molded substrates are typically annealed slowly to provide a flat substrate that mates with a substrate having heat sources with minimal gaps. For example, the injection molded substrate can have a flatness of better than 200 microns, better than 100 microns, or better than 50 microns.

System 99 also includes a plurality of components configured to, e.g., actuate and/or monitor elements of microfluidic device 10. Such components can include heat sources and temperature sensors. During operation of system 99, heat sources and temperature sensors are typically disposed within thermal contact of a localized region of device 10. In some embodiments, the components are integral with device 10, e.g., the components are fabricated within and/or upon one or more substrates that also define the microfluidic network. Alternatively or in combination, the components are fabricated within or upon another portion of system 99, e.g., chip carrier cartridge 20. In use, device 10 and cartridge 20 mate to bring the heat sources and elements of the microfluidic network into thermal communication.

Heat sources can be used to control elements such as thermally actuated fluid control elements, e.g., valves and gates, thermally actuated pumps and vacuum sources, and reaction chambers. For example, a heat source can melt or otherwise increase a mobility of a thermally responsive substance (TRS), e.g., wax, of a thermally actuated fluid control element such as a valve or gate thereby allowing the material to move into or out of an obstructing position in a channel. Heat sources are typically in thermal contact with only a localized portion of device 10 to the extent that one heat source does not actuate more than one element of device 10. System 99 can, however, include heat sources that are in thermal contact with and simultaneously actuate a selected number of elements (more than one element) of device 10. Fluid control elements and TRS's are disclosed in The Processing Application and in U.S. Pat. No. 6,575,188, issued Jun. 10, 2003, which application and patent are incorporated herein by reference.

A temperature sensor can be used to monitor a temperature of a thermally actuated element of device 10, e.g., to determine the temperature of material within a reaction chamber or of a TRS associated with a fluid control element. The temperature sensors generally monitor the temperature within a localized region, e.g., the temperature of a single element, of device 10. System 99 can, however, include temperature sensors that are in thermal contact with several elements of device 10 to simultaneously monitor the temperature of those elements.

In some embodiments, microfluidic device 10 mates with chip carrier cartridge 20 to provide a unit that can be inserted into (or removed from) an interface hardware receptacle of DAQ 26 having electrical and optical contacts 25. The mating can position elements of device 10 within thermal communication of heat sources and temperature sensors of cartridge 20. In such embodiments, cartridge 20 generally includes a pattern of heat sources and temperature sensors that corresponds to a pattern of elements of the microfluidic network of device 10.

The microfluidic device 10 may have electrical and/or optical contacts 12, which connect with the chip carrier cartridge for carrying electrical and optical signals between components of the microfluidic device (if disposed thereon) and the cartridge. The contacts and any leads can be formed with, e.g., wire bonding and photolithography techniques. In some embodiments, device 10 itself includes contacts that mate with a receptacle of DAQ 26.

Alternatively or in combination, the chip carrier cartridge 20 may have electrical and optical contacts 21 for carrying electrical and optical signals between the microfluidic device, the chip cartridge, and contacts 25 of the data acquisition board 26. For example, the cartridge 20 may include components configured to actuate and/or monitor elements of device 10. Contacts 21 can carry electrical and or optical signals between these components and DAQ board 26.

Some of contacts 12, 21, and/or 25 can be configured for electrical signals, while others can be configured for optical signals (IR, visible, UV, etc.) in the case of optically-monitored or optically-excited microfluidic processors. Alternatively (not shown), the entire data acquisition and control board 26 may be a single ASIC chip that is incorporated into the chip carrier cartridge 20, wherein contacts 21, 25 may become lines on a printed circuit board.

In general, DAQ 26 allows control of operation of microfluidic device 10 via contacts 12, 21, 25 using electrical and optical signals. Processor 27 typically performs high level functions, such as supplying a user interface that allows the user to select desired operations and to view the results of such operations. Processor 27 may also include a computer-readable medium comprising code to operate device 10 or a system comprising device 10. As shown in FIG. 2, the processor 27 is connected to DAQ 26 via connection 28, which provides data I/O, power, ground, reset, and other function connectivity. Processor 27 may also be used to control a laboratory robot 24 via link 31. Alternatively, a wireless link 32 between the processor 27 and the DAQ 26 may be provided for data and control signal exchange via wireless elements 32(a) and 32(b). Where the data link is a wireless link, for example, the DAQ 26 may have separate power source such as, for example, a battery.

In some embodiments, the number of components, e.g., heat sources and/or temperature sensors configured to actuate and/or monitor the actuation of various elements of the microfluidic network of device 10, can be large. If each component required one or more dedicated contacts, contacts between a substrate and a chip cartridge, contacts between a chip cartridge and a DAQ receptacle, or contacts between a substrate and a DAQ receptacle, the number of contacts would also be large. The following description of the operation of a microfluidic device 10 and DAQ 26 demonstrates the relationship between the complexity of the microfluidic substrate and the requisite number of contacts 12, 21, 25.

FIG. 3 illustrates, schematically and not to scale, the general structure of an exemplary integrated microfluidic device. This microfluidic device includes a microfluidic network included three types of sub-assemblies. In particular, this microfluidic network has four separate sub-assemblies: two micro-droplet metering sub-assemblies, metering1 and metering2; one mixing sub-assembly, mixing1; and one reaction/detection sub-assembly, reaction/detection1.

These sub-assemblies are constructed from elements such as valves, pumps, vents, passages, space to accommodate overflows, reservoirs, inlets, outlets detectors, mixing zones, and the like. For example, sub-assembly metering1 includes inlet1, overflow1, valve1, heater1, and passage1. Similarly, sub-assembly metering2 includes inlet2, overflow2, valve2, heater2, and passage2. The mixing subassembly, mixing1, includes heater1, heater2, valve3, valve4, vent1, vent2, Y-shaped passage3, and passage4. Finally, reaction/detection1 sub-assembly includes valve5, valve6, heater3, and passage5.

Some elements of device 10, e.g., valves, pumps, reaction chambers, detection and chambers, can be actuated and/or monitored using components of system 99. Operations of the sub-assemblies generally result from the coordinated operations of their component actuators under the control of an external controller, DAQ 26, which preferably operates in accordance with instructions from code of a computer-readable medium. The specific operation of microfluidic device 10 is described in greater detail in co-pending application Ser. No. 09/819,105, which is incorporated herein by reference. However, the following describes exemplary operation of the fluid processor under the control of DAQ 26.

First, fluid is introduced into inlet1, for example, by an external robotic device, and flows up to the stable position created by the first hydrophobic region h3 just beyond the widening of passage1. Any excess fluid flows out through port overflow1. Next, DAQ 26 instructs sub-assembly metering 1 to measure a micro-droplet of determined volume from an aliquot of fluid introduced through port inlet1, as described in co-pending application Ser. No. 09/819,105. Sub-assembly metering2 is constructed and operates similarly to extract a measured micro-droplet of fluid from a second fluid sample likewise supplied at inlet 2.

After the pair of microdroplets are extracted from the inlet ports, DAQ 26 supplies current to heater1 and heater2 to generate gas pressure to propel the two micro-droplets through Y-shaped passage3 and along passage4 to the stable position in passage5 just beyond the junction of the side passage to vent2. During this step, the two microdroplets merge and mix to form a single, larger micro-droplet.

Next, DAQ 26 supplies current to valve5 and valve6 to close these valves and isolate the micro-droplet along passage5. DAQ 26 directs the sub-assembly reaction/detection1 to stimulate a reaction in the trapped micro-droplet by, for example, supplying current to heater3, which heats the micro-droplet. The DAQ then monitors the results of the stimulated reaction by optically detecting radiation conducted by optical paths o1 and o2. DAQ 26 performs these control functions by selectively supplying electrical (and sometimes optical) signals to the microfluidic substrate via contacts 12, 21, 25.

DAQ Board Architecture

Figure 4:
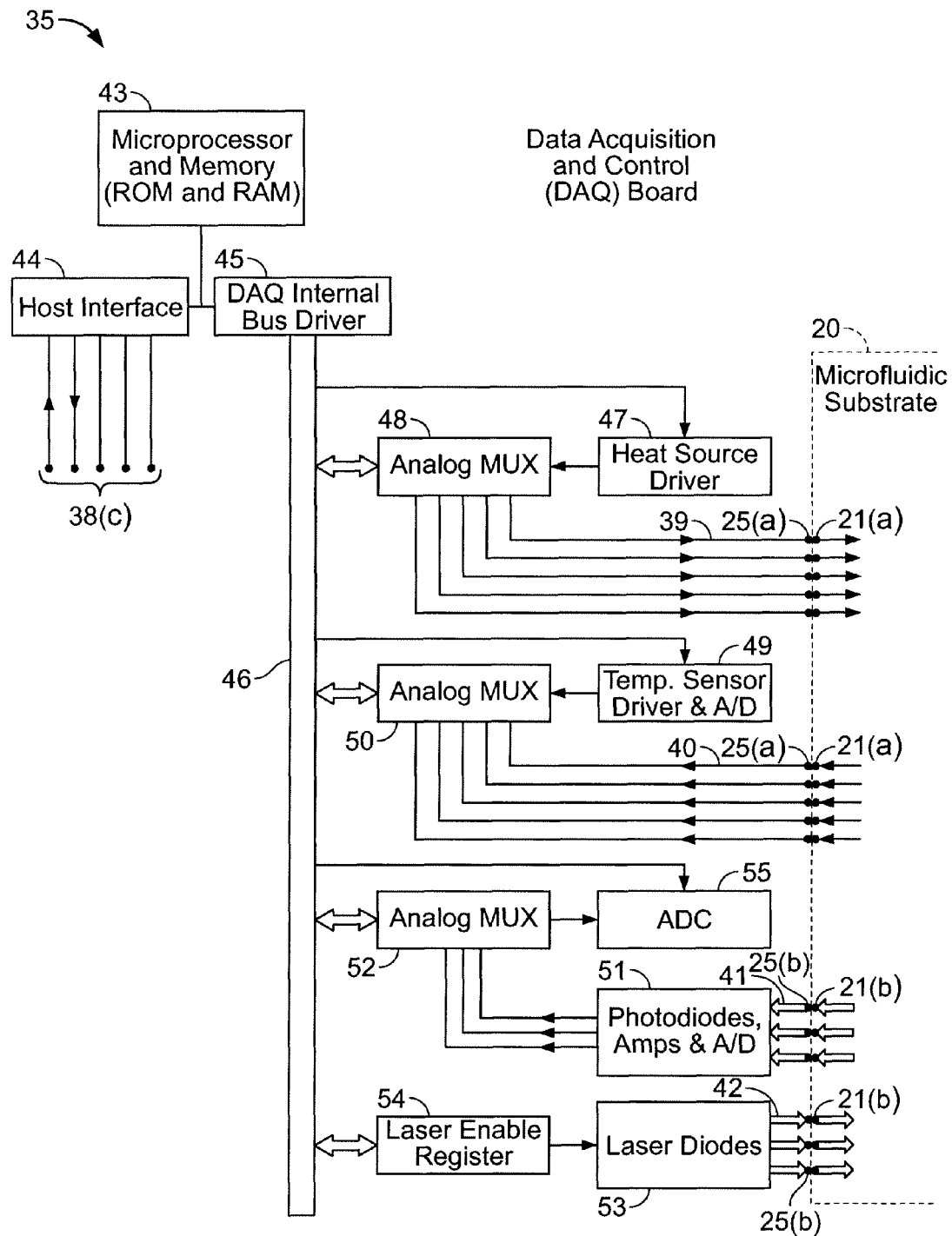
FIG. 4 illustrates the external controller of FIG. 2.

FIG. 4 illustrates an embodiment of hardware architecture for DAQ board 26. The DAQ board has one or more receptacles, slots, or sockets, where one or more replaceable microfluidic devices may be accommodated in a firmly supporting manner with good contact to its external contacts. In some embodiments, the DAQ board accommodates or includes a chip cartridge including a plurality of heat sources. The microfluidic device mates with the chip cartridge to place the heat sources and thermally actuated components of the microfluidic device in thermal communication.

As shown, electrical contacts 25(a) on the DAQ mate with corresponding contacts 21(a) of the chip carrier cartridge 20. Thus, leads 39, 40 of the DAQ are electrically connected to corresponding leads of the chip carrier cartridge 20. Similarly, contacts 25(b) of the DAQ mate with contacts 21(b) of the chip carrier cartridge, thereby connecting via light pipe, line of sight, or by other suitable means, the DAQ's optical couplings 41,42 to corresponding optical couplings on the chip carrier cartridge. The electrical and optical leads of the chip carrier cartridge are, in turn, connected to the microfluidic device 10 via contacts 12. Thus, DAQ 26 can send and receive electrical and optical signals via contacts 12, 21, 25 to and from microfluidic device 10 in order to engage and control a variety of components or actuators located on cartridge 20 and/or device 10.

The electrical contacts, which may have many embodiments, are illustrated here as edge contacts that are engaged when the chip carrier and microfluidic substrate are inserted in a DAQ board receptacle. Alternatively, contacts may be suitable for engaging a flexible ribbon cable, or may by multi-pin sockets, for example. The optical contacts may be of types known for connecting fiber-optic cables.

The DAQ may include one or more electrical energy sources such as heat source drivers 47 for supplying a specified amount of current and/or a particular voltage. The output of each heat source driver 47 may be connected to an analog multiplexer 48 that routes the current from the driver to a selected I/O contact 25(a). For thermal sensing functions, the DAQ may include one or more electrical energy sources such as temperature sensor drivers 49 which are each connected to an analog multiplexer 50 that multiplexes each temperature sensor driver 49 to a selected one of the plurality of I/O contacts 25(a).

In some embodiments, heating and sensing functions are provided by a single element, such as a component with temperature dependent resistance. Such combined elements can be operated by an electrical energy source, e.g., a voltage or current supply. Typically an electrical energy source is configured, in a first actuation state, to provide current or electrical potential sufficient to heat the resistive component. The energy to heat the resistive component is generally sufficient to heat an element (e.g., a TRS and/or pressure chamber of a valve, a TRS of a gate, reaction chamber contents, or a gas actuated pump) of microfluidic device 10 in thermal contact with the resistive component. In a second activation state, the electrical energy source provides a current or electrical potential sufficient to operate a sensing function of the component. The actuation state of the one or more electrical energy sources driving a combined heating sensing component may be determined by code of a computer readable medium.

The DAQ 26 can include one or more photodiodes 51 for optical detection. Multiplexor 52 multiplexes signals from and to these optical detectors to an analog-to digital converter ("ADC") 55 via a selected one of the plurality of I/O contacts 25(b). Finally, the DAQ is shown as controlling one or more laser diodes 53. Laser enable register 54 enables selected laser diode drivers, thereby emitting light signals on corresponding optical couplings 42 and optical contacts 25(b).

Also shown in FIG. 4, the DAQ also includes a microprocessor and memory 43 for controlling the operation of the drivers 47, sensors 49, photo diodes 51, laser diodes 53 and their associated analog multiplexors 48, 50, 52, as well as laser enable register 54. More specifically, the microprocessor sends control signals to these devices via a bus driver 45 and bus 46, and reads status information from the sensing elements via the same driver 45 and bus 46. Finally, host interface 44 allows the microprocessor 43 to communicate with the general purpose processor 27 (FIG. 2) via leads 38(c) or, as described above, via wireless means.

The operation of the DAQ is exemplified by the following description of the control of a simple resistive heat source, such as the resistive heater shown in valve 1 of the microfluidic device depicted in FIG. 3. As shown in FIG. 3, valve 1 includes a resistive heating element 9 that is connected at its terminals 11, 13 to a pair of I/O contacts 12(a) via leads 8. The DAQ activates this resistive heating element by instructing analog multiplexor 48 to connect the output of heat source driver 47 to a pair of I/O contacts 25(a) that are connected to corresponding 1/0 contacts 21(a) of the chip carrier 20, that are connected to corresponding contacts 12(a) of the substrate. It then instructs heat source driver 47 to supply a selected amount of current. The current supplied by driver 47 flows through analog multiplexor 48 and to the resistive heating element 9 via the selected leads 39 and 8.

Figure 5A:
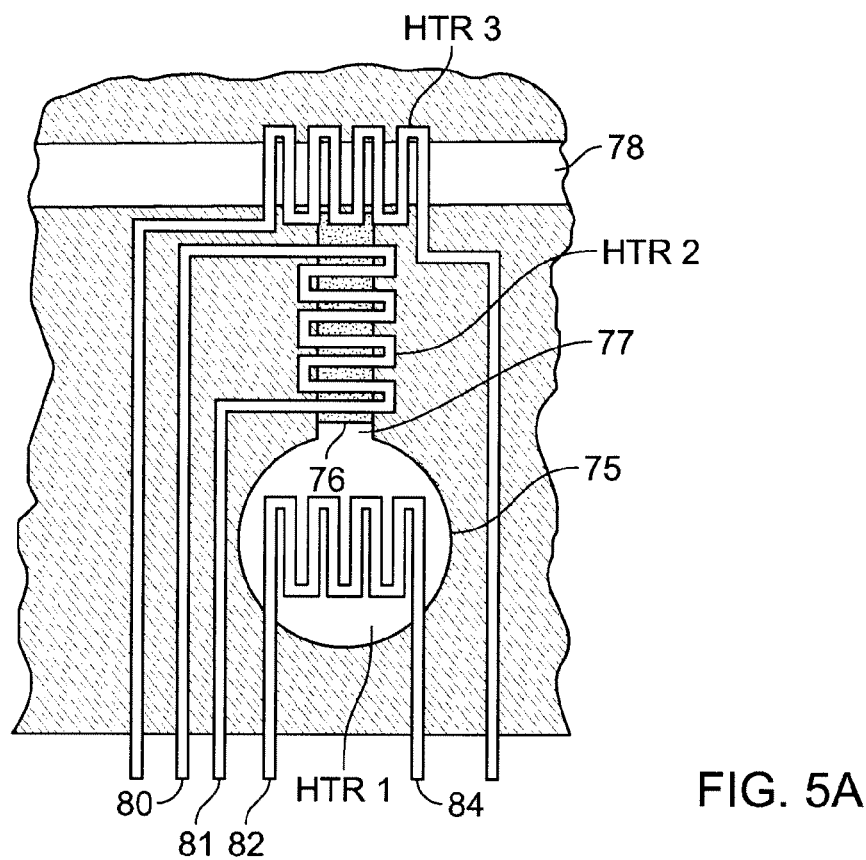
FIG. 5A is a micro-valve actuator in an open state.
Figure 5B:
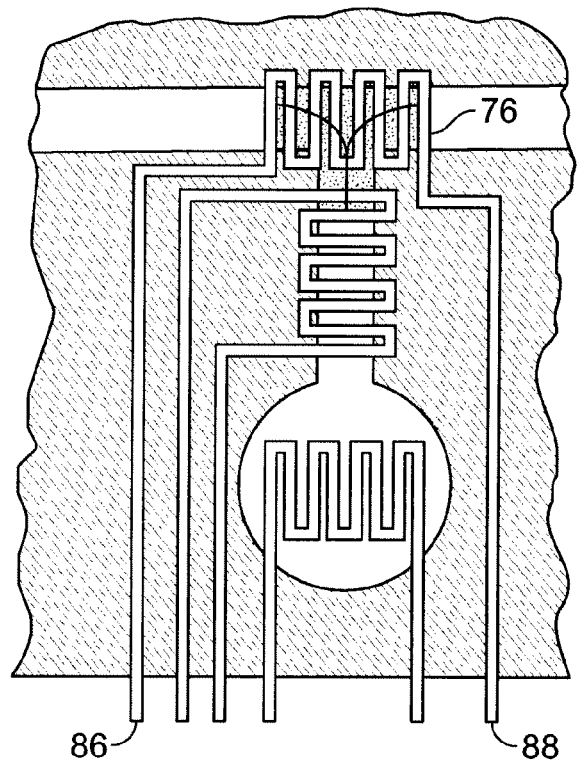
FIG. 5B is the micro-valve actuator of FIG. 5A in a closed state.

Referring to FIGS. 5A and 5B, an exemplary operation of a fluid control element, e.g., a valve, is described. FIG. 5A depicts the valve in its open position, having a mass of TRS, e.g., a wax plug 76, positioned within side channel 77. The mass of TRS can have a volume of about 250 nanoliters or less, about 125 nl or less, e.g., about 75 nl or less. To close this valve, DAQ controller supplies current to resistive heater HTR2 via I/O contacts 80, 81. This causes HTR2 to warm, thereby melting plug 76. DAQ 26 then supplies current to HTR1 via I/O contacts 82, 84 to thereby heat gas within chamber 75. As the gas expands, it forces plug 76 to move into channel 78 as shown in FIG. 4B. DAQ 26 then shuts off heater HTR2 and allows the plug to cool, thereby blocking channel 78 and side channel 77. When the plug is cool, DAQ 26 shuts off HTR1. As HTR1 cools, the pressure in chamber 75 drops, thereby creating a negative pressure which, as will be explained below, may be used to re-open the valve.

To open the valve, DAQ 26 supplies current to HTR3 via I/O pins 86, 88 to warm the heater and thereby melt the plug. Once the plug is melted, the negative pressure in chamber 75 draws the plug back into side channel 77, thereby re-opening channel 78.

In some embodiments of a fluid control element, some or all of the mass of TRS moves downstream upon opening the control element. Such fluid control elements are referred to as gates.

FIGS. 6A and 6B-6D depict heating and sensing components suitable for use in microfluidic devices, such as to open or close valves, e.g., as discussed with respect to FIGS.

5A/5B, heat reaction mixtures present in reaction chambers, or provide a material transport function, such as by actuating a thermally actuated pump.

Figure 6A:
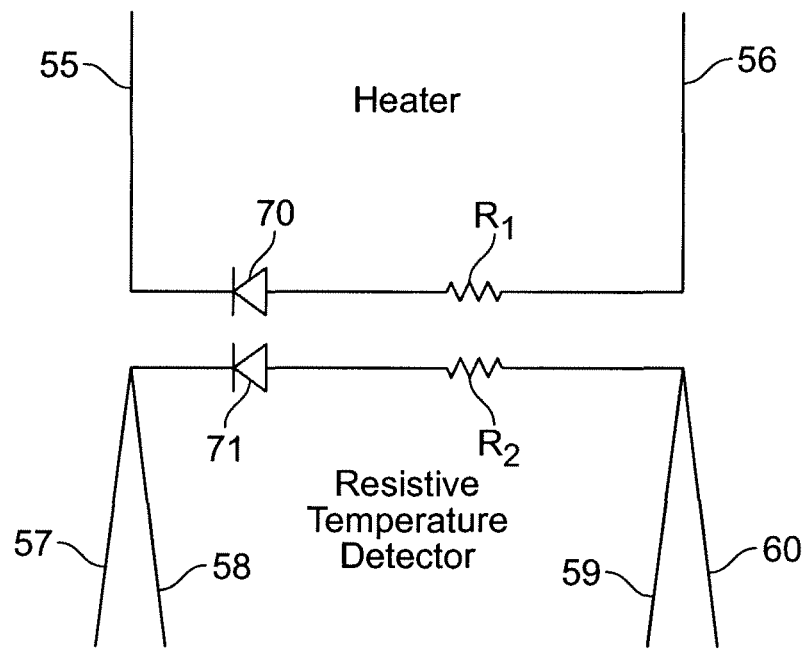
FIG. 6A is a heat source having a separate resistive temperature sensor.

FIG. 6A depicts a six-terminal resistive heating and sensing component. The component includes a two terminal heat source R1 that operates in accordance with heat source 9 of FIG. 2. The device also includes a current flow directional element 70, which allows current to flow substantially only in a single direction between leads 55, 56 of heat source R1. As shown in FIG. 6A, current flow directional element 70 is a diode configured to allow current to flow from lead 56 to lead 55. Current flow directional element 70 substantially prevents, and preferably excludes, current flow from lead 55 to lead 56. Current flow directional element 70 may be any element that allows current to flow predominately in one direction between points of a circuit. Current flow directional elements are typically diodes.

The device of FIG. 6A also includes a four terminal temperature sensor, e.g., a resistive sensor component R2 in close proximity to R1 so as to be in thermal communication therewith. A current flow directional element 71, which has the generally the same functional characteristics as current flow directional element 70, allows current to flow in substantially one direction between leads 57, 58 and leads 59, 60 of resistive sensor component R2. In the configuration shown, current flow directional element 71 allows current to flow from leads 59 and 60 to leads 57 and 58 but substantially prevents, and preferably excludes, current flow from leads 57 and 58 to leads 59 and 60.

Current flow directional elements 70 and 71 may be but are not necessarily formed by microfabrication on a substrate with elements R1 and R2. Rather, current flow directional elements 70 and 71 may be disposed at other positions along current path ways that respectively include R1 and R2. Current flow directional elements 70 and 71 are generally disposed in series with R1 and R2.

The sensor R2 may operate as follows. While DAQ 26 supplies current to R1 (via leads 55,56) it also supplies a relatively low current to R2 via leads 57,60. R2 is a resistive component whose resistance generally increases with temperature. Accordingly, the voltage across R2 increases with the temperature in the nearby region being heated by heat source R1. Therefore, component R2 can be used to measure the temperature in this region. DAQ 26 determines the temperature by measuring the voltage across R2 via leads 58, 59. More specifically, referring now to FIG. 4, DAQ 26 instructs the analog multiplexor to connect temperature sensor 49 to the contact pins 25(a) which are connected to leads 58, 59. Sensor 49 then determines the voltage across R2, thereby providing a measure of the temperature in the vicinity of R1.

The Relationship Between the Number of I/O Contacts and the Number of Components Actuating and/or Monitoring Elements of the Microfluidic System For a two terminal component, such as the resistive heater RI described above, the system may use two I/O contacts to supply the control signals for operation of the component. Thus, if the number of two-terminal components of system 99 is N, then 2N I/O contacts are sufficient to allow DAQ 26 to independently control each of the components.

However, for complex microfluidic devices, the number of I/O contacts can become large. In the microfluidic device shown in FIG. 3, where only nine different resistive heat sources are shown, eighteen contacts are required. For increasingly complex microfluidic devices having hundreds of independently controlled components, the number of contacts becomes larger.

Techniques for reducing the number of I/O contacts required for an external controller, such as DAQ 26, to independently control a large number of components of a microfluidic device are discussed below.

Combined Heating Temperature Sensing Components

Figure 6B:
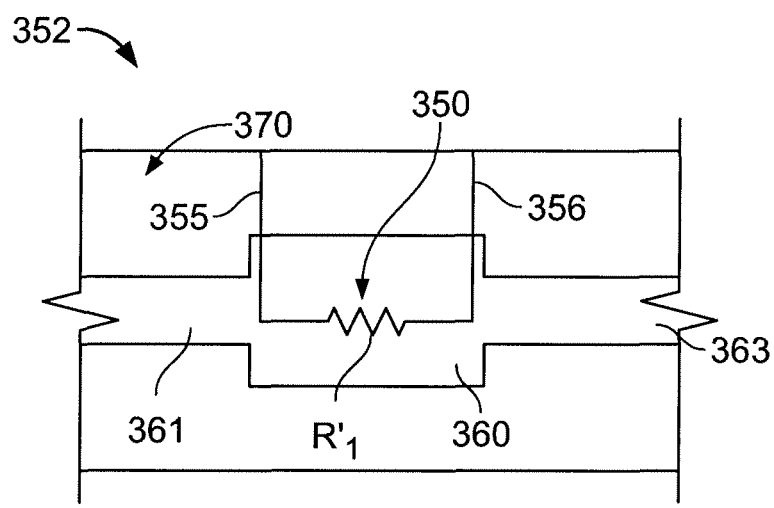
FIG. 6B is a top view of a microfluidic reaction chamber with a combined heat source temperature sensor in thermal communication therewith.
Figure 6C:
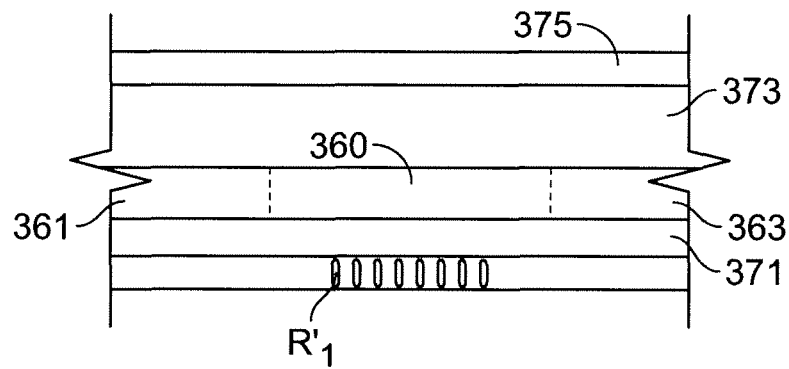
FIG. 6C is a side view of the microfluidic reaction chamber and combined heat source temperature sensor of FIG. 6B.

Referring to FIGS. 6B and 6C, a combined heating/temperature sensing component 350 is operable both as a heat source and as a temperature sensor. Component 350 is shown in thermal communication with a thermally actuated component of a microfluidic device 352, only a portion of which is shown. FIGS. 6B and 6C do not illustrate other components, such as other microfluidic elements, modules, passages, pumps, valves, reaction chambers, access ports, and the like that microfluidic device 352 may include.

The thermally actuated component is, by way of an example only, a reaction chamber 360 having an upstream channel 361 and a downstream channel 362. It should be understood that such thermally actuated components are not limited to reaction chambers but can include, e.g., a pressure actuators or fluid control elements.

Device 352 includes a substrate 370, which typically includes first and second substrate portions 371, 372 defining a microfluidic network including microfluidic element 360 therebetween. Device 352 can also include a third substrate portion 375. Exemplary microfluidic devices are discussed in The Processing Application.

Combined heating/temperature sensing component (CHTSC) 350 includes a component R1', which, in a first actuation state, generates thermal energy to maintain or increase a temperature of the microfluidic element, e.g., material within chamber 360, and, in a second actual state, may be used to obtain electrical property data indicative of a temperature of component R1'. Exemplary components R1' include temperature-dependent resistors and elements including junctions between two dissimilar materials. The device 350 also includes leads 355 and 356 by which electrical energy may be supplied to element R1'. Leads 355,366 and element R1' form an electrical pathway comprising element R1', which is disposed in thermal communication with the microfluidic element 360. An electrical energy source may be used to place an electrical potential across element R1' via leads 355,366.

Device 10 or a system configured to operate device 10 may include an electrical measurement device, for example, an ammeter, configured to provide data indicative of an electrical characteristic, such as a current, power dissipation, or electrical potential drop, of the resistive component.

Figure 6D:
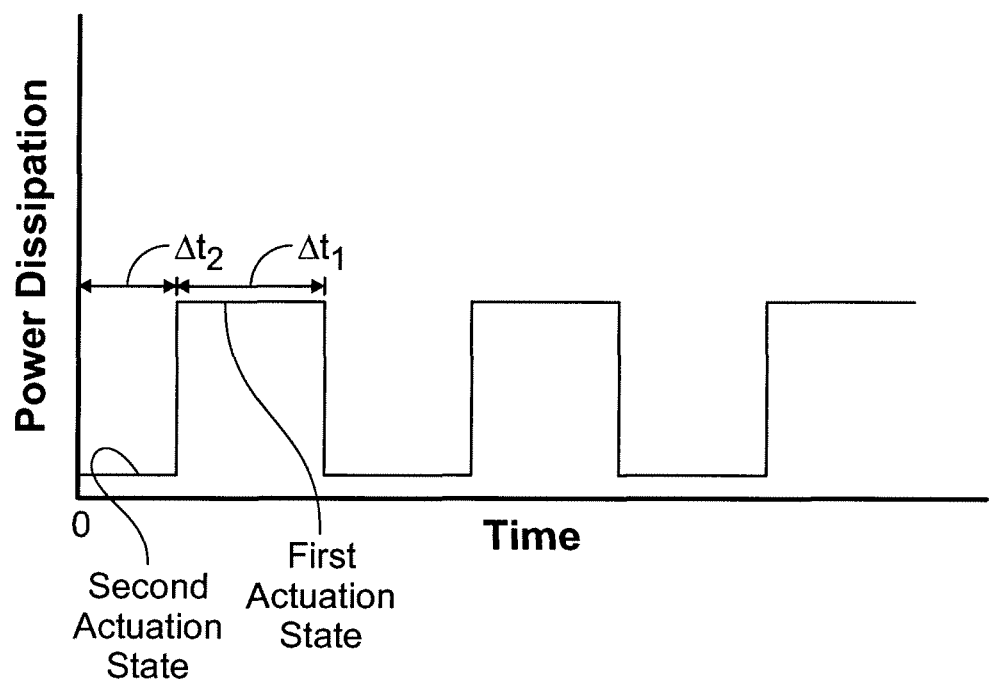
FIG. 6D is a power dissipation versus time plot of the combined heat source temperature sensor of FIG. 6B.

Referring to FIG. 6D, an exemplary operation of combined/heater sensor R1' is illustrated using a plot of power dissipation by R1' as a function of time. Power dissipation is indicative of the amount of energy dissipated per unit time by the CHTSC. The heating/temperature sensing component can be operated under the control of code of a computer-readable medium.

In use, microfluidic devices and/or microfluidic systems comprising CHTSC components typically include one or more electrical energy sources in electrical communication with the CHTSC. The system includes a computer-readable medium having code to operate the one or more electrical energy sources. For example, the computer readable medium may include code to provide first and second actuation states of an electrical energy source in electrical communication with the CHTSC. During the first actuation state, a first electrical current flows through the CHTSC, e.g., through a resistive component or dissimilar metal junction thereof. During the second actuation state, a second, lower electrical current flows through the CHTSC.

During the second actuation state, current can be supplied to the CHTSC to determine an electrical property thereof, e.g., a resistance thereof. The current during the second actuation state does not heat the CHTSC to a temperature exceeding the temperature of the CHTSC immediately prior to initiating the second actuation state. The voltage across the CHTSC, produced by the current, can be sampled, such as by a traditional sample and hold amplifier, which may be configured to sample only during the second actuation state. The output of the sample and hold amplifier may then be fed to an analog to digital converter which may generate temperature data used for system feedback and control.

The CHTSC and microfabricated element 360 may be characterized by a dissipation constant (DC) having units of power per degree, for example watt/° C. If a microfabricated device comprising a CHTSC of the invention (a) is at an ambient temperature of about 20° C. and (b) the CHTSC dissipates an amount of power k, the temperature of at least a portion of the microfluidic element in thermal contact with the CHTSC typically rises to and/or is maintained at a temperature T=k/DC. For example, given sufficient time, e.g., about 60 seconds, a CHTSC in thermal communication with a reaction chamber, typically heats substantially all of the material, e.g., a PCR mixture or other materials, in the chamber to a temperature k/DC. Given sufficient time, e.g., about 60 seconds, a CHTSC in thermal communication with a thermally responsive material, e.g. a wax, of a valve, typically heats substantially all of the material to a temperature k/DC.

It should be understood that the duration of a single first actuation state may be insufficient to raise the temperature of the microfluidic element to the temperature k/DC. Repeated first actuation states may be performed. In general, first actuation states are separated by second actuation states, during which, a temperature sensing function is performed.

During a first actuation state, the CHTSC dissipates an amount of power k1. The ratio k1/DC is typically about 30° C. or more, such as about 50° C. or more, about 55° C. or more, for example, about 60° C. or more, or about 65° C. or more. The ratio k1/DC may be about 100° C. or less, such about 95° C. or less, for example, about 85° C. or less.

In one embodiment, sufficient power is dissipated during the first actuation state (or upon repeated applications of the first actuation state) that the temperature of liquids within a microfluidic reaction chamber in thermal contact with the CHTSC would rise to a temperature sufficient to support amplification of polynucleotides present in the liquids. The first actuation state (or the repeated first actuation states) may generate sufficient thermal energy to heat at least the portion of the microfluidic element in thermal contact with the CHTSC to about 30° C. or more, such as about 50° C. or more, about 55° C. or more, for example, about 60° C. or more, or about 65° C. or more. In the first actuation state (or the repeated applications thereof), the portion of the microfluidic element in thermal contact with the CHTSC is generally heated to less more than 200° C., less than 150° C., less than 100° C., less than 95° C., for example, less than 85° C.

During a second actuation state of the CHTSC, the component may dissipate an amount of power k2, which is preferably smaller than k1. For example, if the second actuation state follows the first actuation state in time, the temperature of the CHTSC and or the microfluidic element in thermal contact therewith may fall during second actuation state from a temperature attained during the first actuation state. If the first actuation state follows a second actuation state, the temperature may rise during the first actuation state as compared to the temperature immediately preceding the initiation of the first actuation state. The ratio k2/DC is preferably about 50° C. or less, such as about 45° C. or less, for example, about 40° C. or less, about 35° C. or less, or about 30° C. or less.

As shown in FIG. 6D, the code may operate the electrical energy source in the second actuation state for a time $\Delta\tau 2$. The code may operate the electrical energy source in the second actuation state for a time $\Delta\tau 1$. The power dissipated need not be constant during each actuation state. The power dissipated need not be the same between successive first actuation states or successive second actuation states. In one embodiment, the amount of power dissipated during the second actuation state and the duration of the second actuation state are such that the absolute temperature of the microfluidic element in thermal contact with the CHTSC falls by less than 5%, for example less than 2.5%, of the maximum temperature reached during a preceding first actuation state. For example, the absolute temperature of a reaction mixture in a reaction chamber in thermal contact with a CHTSC may fall by less than less than 5%, for example less than 2.5%, of the maximum temperature reached during a preceding first actuation state.

The lengths of the first and second actuation states may be different. The lengths of successive first actuation states and successive second actuation states may be different. In some embodiments, first actuation states are shorter than 60 seconds, shorter than 45 seconds, shorter than 15 seconds, shorter than 1 second. Second actuation states may be the same length as first actuation states or shorter. For example, second actuation states may be 5 seconds or less, 1 second or less, 0.1 seconds or less, or 0.01 seconds or less.

In some embodiments, the second actuation states have a duty cycle of no more than about 5%, no more than about 2.5%, no more than about 0.5%, no more than about 0.25%, or no more than about 0.2% and the first actuation states have a duty cycle of no more than 90%, no more than 95%, no more than 97.5%, or no more than 99% During a remaining portion of the duty cycle, if any, the system is neither in the first nor the second duty cycle. This remaining portion may be used to stabilize a circuit that determines an electrical property of the heater/sensor, e.g., a voltage drop thereacross. For example, this circuit may include a diode clamp that is stabilized during the remaining portion of the duty cycle. In some embodiments, during the remaining portion, no current is passed through the heater sensor.

The computer-readable medium typically includes code to sense an electrical property of the CHTSC, determine a temperature from the sensed property, compare the temperature to a selected temperature, and use the result of the comparison in a feedback loop to adjust further heating and temperature sensing steps. Examples of such code are discussed below.

The computer-readable medium may include code to receive data indicative of an electrical property of the CHTSC, such as of a resistive component thereof, from the electrical measurement device. The data indicative of the electrical characteristic of the resistive component may be indicative of a temperature-dependent resistance of a resistive component of the CHTSC. In some embodiments, the data indicative of the electrical characteristic of the resistive component is indicative of an electrical potential required to cause a predetermined current to flow through the CHTSC. The data indicative of the temperature-dependent electrical characteristic of the CHTSC may be obtained while the electrical energy source is in the second actuation state.

The computer-readable medium may comprise code to determine a temperature of the resistive component based on the data indicative of the electrical property. The data may be indicative of the electrical characteristic of the resistive component when the electrical energy source is in the second actuation state. There may be code to compare the temperature of the resistive component with a predetermined temperature value, and, optionally, code to repeat the first and second actuation states of the electrical energy source if the temperature is less than the predetermined temperature value. The medium may comprise code to repeatedly determine the temperature of the CHTSC, compare the temperature of the CHTSC with the predetermined temperature value, and repeat the first and second actuation states of the electrical energy source, the determination of temperature, and the comparison of temperature and the predetermined temperature value if the temperature is less than the predetermined temperature value. The computer-readable medium may comprise code to vary, at least once, at least one of the first and second currents when repeating the first and second actuation states of the electrical energy source.

The computer-readable medium can include code to compare, based upon the received data indicative of the electrical characteristic, (i) a current flowing through the CHTSC, e.g., during the second actuation state, and (ii) a predetermined current. The medium can include code to increase an electrical potential across a portion of the CHTSC, such as a resistive component thereof, during the second actuation state if the second, lower current is less than the predetermined current. There may be code to decrease an electrical potential across the CHTSC during the second actuation state if the second, lower current exceeds the predetermined current. There may be code to receive electrical potential data (e.g., from an electrical energy source) indicative of the electrical potential across the CHTSC during the second actuation state if the second, lower current is within a predetermined range of the predetermined current. The computer-readable medium may comprise code to determine the temperature of the CHTSC based on the electrical potential across the CHTSC when the second, lower current is within the predetermined range of the predetermined current.

The computer-readable medium may comprise code to provide the first actuation state of the electrical energy source if the temperature of the resistive component is less than a predetermined temperature. The computer-readable medium may comprise code to repeatedly determine the temperature of the CHTSC, such as a resistive component thereof, based on the electrical potential across the CHTSC when the second, lower current is within the predetermined range of the predetermined current and provide the first actuation state of the electrical energy source if the temperature of the CHTSC is less than the predetermined temperature.

Multiplexed Actuation of Heat Sources and Other Components

Figure 7A:
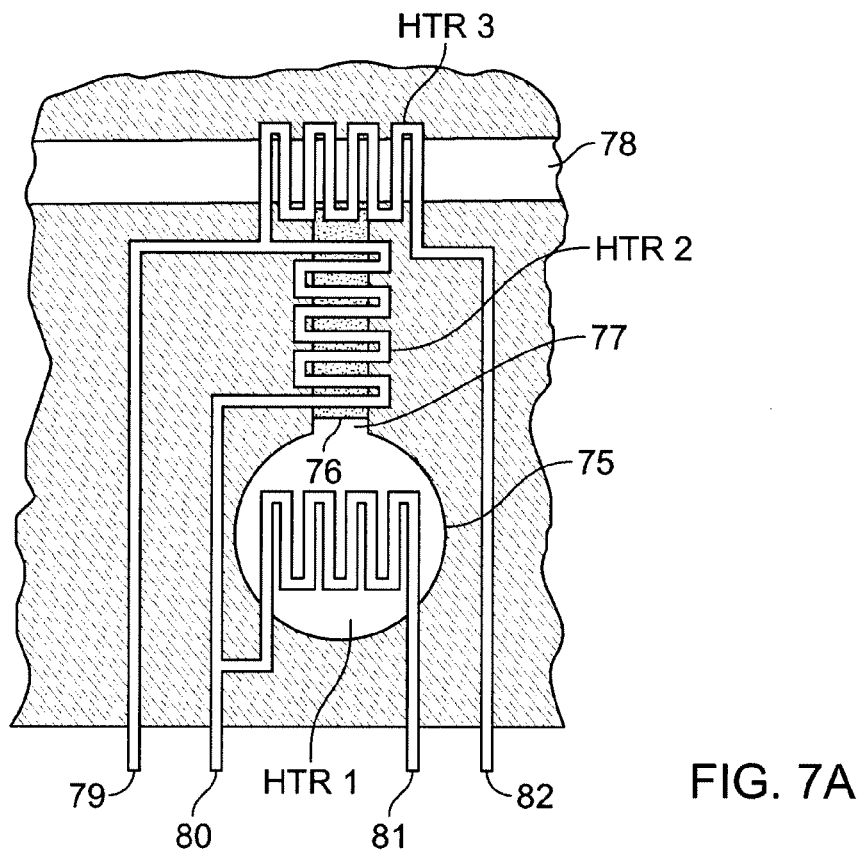
FIGS. 7A-B illustrate a micro-valve actuator having a reduced number of I/O contacts, with the valve being in the open state in FIG. 7A and in the closed state in FIG. 7B.
Figure 7B:
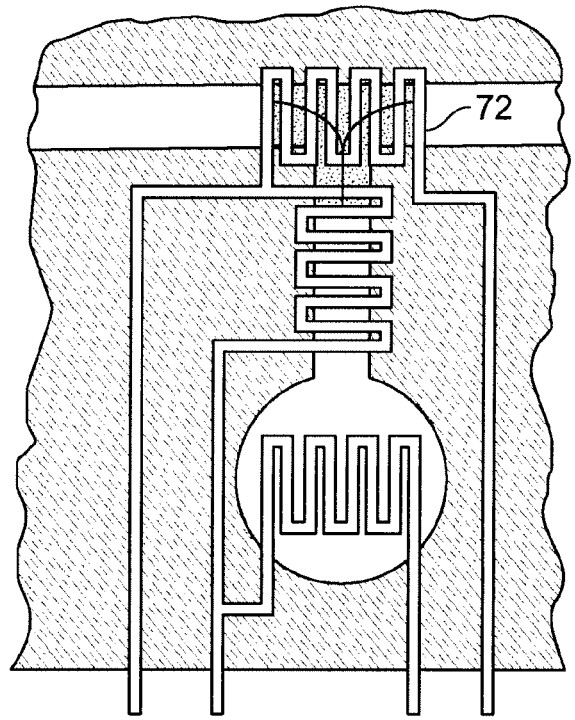

FIGS. 7A, 7B illustrate a technique for reducing the number of 1/0 contacts by structuring the leads that provide current to the heat sources, temperature sensors, or combined heat source/sensors of the microfluidic device so that each lead serves more than one component, while still allowing DAQ 26 to control each thermally actuated component of the microfluidic device independently of others. Specifically, FIGS. 7A, 7B depicts a technique for sharing I/O contacts among three of the two-terminal resistors of a valve structure, such as shown in FIGS. 5A-5B discussed above. The valve operates essentially the same as the valve shown in FIGS. 5A, 5B, except that it uses only four contacts rather than six. In this example, each resistor is connected to a pair of I/O contacts and therefore can be controlled by the DAQ in the same way as described above. Although the other resistors share these I/O contacts, no resistor shares the same pair of contacts with another. Accordingly, the DAQ is able to supply current to any given resistor via the pair of associated contacts, without activating any other resistor.

More generally, the number of I/O contacts required for the independent control of a plurality of heat sources, e.g., resistive heaters, may be reduced by arranging the contact wiring to each resistor in the form of a logical array. The resulting compression of the number of I/O contacts advantageously simplifies communication with the entire processor. Because each resistor requires two leads to complete an electrical circuit, according to a conventional arrangement of leads and contacts, a device having N resistors requires 2N leads and 2N contacts. By configuring the contact wiring in a shared array, however, the number of required contacts can be reduced to as few as 2N1/2. For example, in a device comprising 100 resistors, the number of external contacts can be reduced from 200 to 20.

Figure 8A:
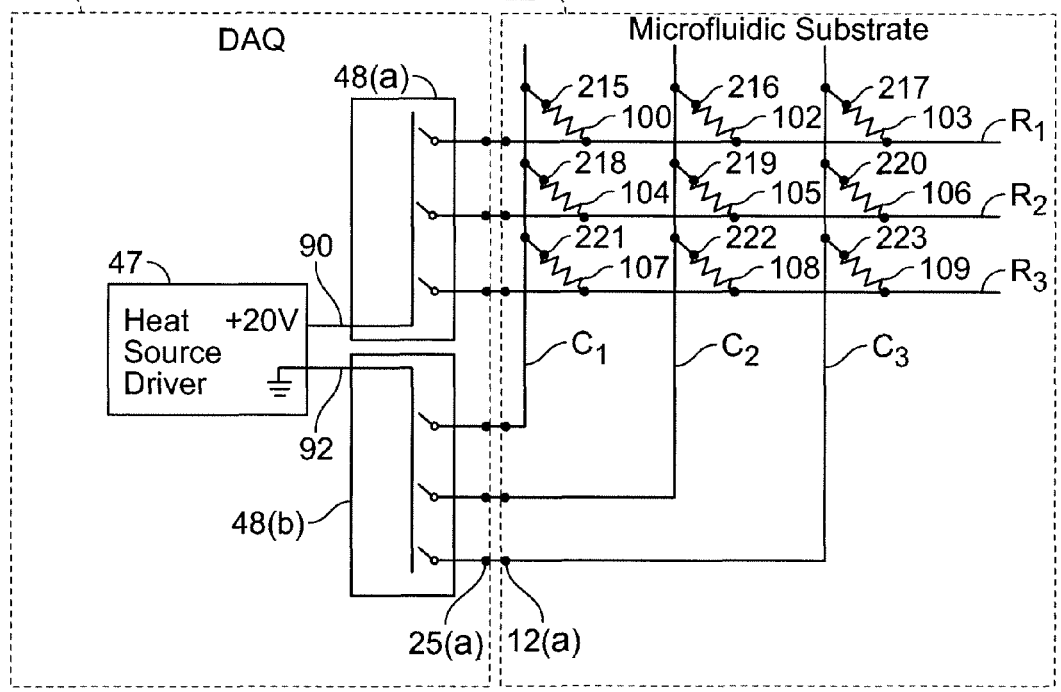
FIGS. 8A-B illustrate a technique for sharing conductive leads that supply current to resistive heat sources in thermal communication with a microfluidic device.
Figure 8B:
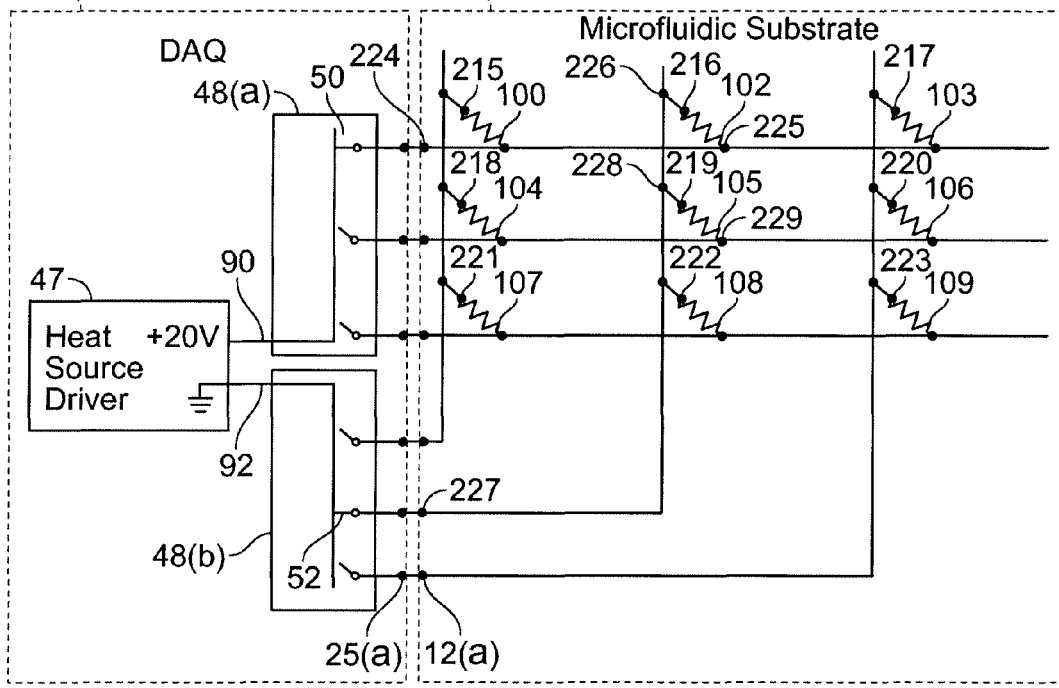

FIGS. 8A, 8B depict a DAQ 26 directly connected to a microfluidic substrate 22, without the use of an intermediate chip carrier 20, and show an array of resistive heaters within substrate 22. The leads between contacts 12($a$) and resistive heaters 100-109 are shown arranged in columns and rows. However, the actual physical layout of the leads will not necessarily be a physical array. Rather, the leads may be directly routed from the resistive components to contacts 12($a$) in any manner that allows each lead to connect to a plurality of resistors while remaining electrically isolated from other leads.

According to this arrangement, electrical contacts for N resistors can be assigned to R rows and C columns such that the product RC is greater than or equal to N. Typically, R is approximately equal to C, and generally equals C. With this arrangement, resistors assigned to the same row share a common electrical lead and I/O contact 12($a$). Similarly, resistors assigned to the same column also share a lead and I/O contact 12($a$). However, each resistor has a unique address, corresponding to a unique pair of I/O contacts, (e.g., to its unique row/column combination in the array), Therefore, each resistor is individually actuatable by supplying electric current to the appropriate pair of I/O contacts.

As used herein, a "resistor" or "component" that is uniquely associated with a pair of contacts may also refer to a resistive network (having a plurality of resistive sub-components contacted in series and/or parallel) or a component network (having a plurality of sub-components connected in series or parallel). In such embodiments, all sub-components are activated together when the external controller supplies signals across the pair of contacts uniquely associated with those sub-components.

As shown in FIG. 8A, the leads are arranged in three rows ($R_j$, where by way of example j=1-3) and three columns ($C_i$, where by way of example i=1-3). For each resistor, one terminal is connected to a row and the other terminal is connected to a column. Although each resistor shares these leads with other resistors, no two resistors share the same pair of leads. In other words, each resistor is uniquely associated with a particular row/column pair $R_j$, $C_i$. FIGS. 8A, 8B illustrate the operation of this structure. Heat source driver 47 supplies an output voltage of twenty volts on its terminals for supplying current to heating elements 100-109.

The positive output terminal 90 is connected to a first analog multiplexor 48(a). As shown, this terminal can be connected to any one of the rows of the array of leads by individual switching elements within analog multiplexor 48(a). Similarly, the negative output terminal 92 of heater 47 is connected to a second analog multiplexor 48(b). Multiplexer 48(b) allows terminal 92 to connect to any column in the array of leads.

In FIG. 7B, the switching elements within analog multiplexors 48(a,b) are all open. Accordingly, none of the heating elements 100-109 as shown are active. FIG. 8B depicts the condition of analog multiplexors 48(a,b) after DAQ 26 has instructed them to close certain internal switches to thereby supply current to a selected one of the resistors in the array. In this example, the row switch element 50 is closed, to thereby connect the positive terminal of heater 47 to the top row of the lead array. The column switch element 52 is also closed to connect the negative terminal of heater 47 to the middle column of the lead array. Thus, the positive terminal 90 of heater 47 is connected to resistors 100,102,103 and the negative terminal is connected to resistors 102,105,108. However, only one of these resistors, 102, is connected across both terminals of heater 47. Accordingly only resistor 102 receives current and is heated.

Resistors heaters 100-109 are disposed in series with respective current flow directional elements 215-223, which allow current to flow in one direction between the positive terminal 90 of a heat source driver 47 and a negative or ground terminal 92 of heat source driver 47 along a current path that includes one of resistive components 100-109. Current flow directional elements 215-223 are typically configured allow current to flow only from positive terminal 90 to terminal 92. Thus, for example, current may flow from a point 224 to a point 225, through resistive heater 102 to point 226 and then to point 227. The current flow directional elements, however, prevent current from passing through current pathways including resistive heaters other than resistive heater 102. For example, current flow directional element 219 prevents current flow between points 228 and 229. Current flow directional elements 215-223 may be diodes as discussed above for current flow directional elements 70, 71.

Figure 9A:
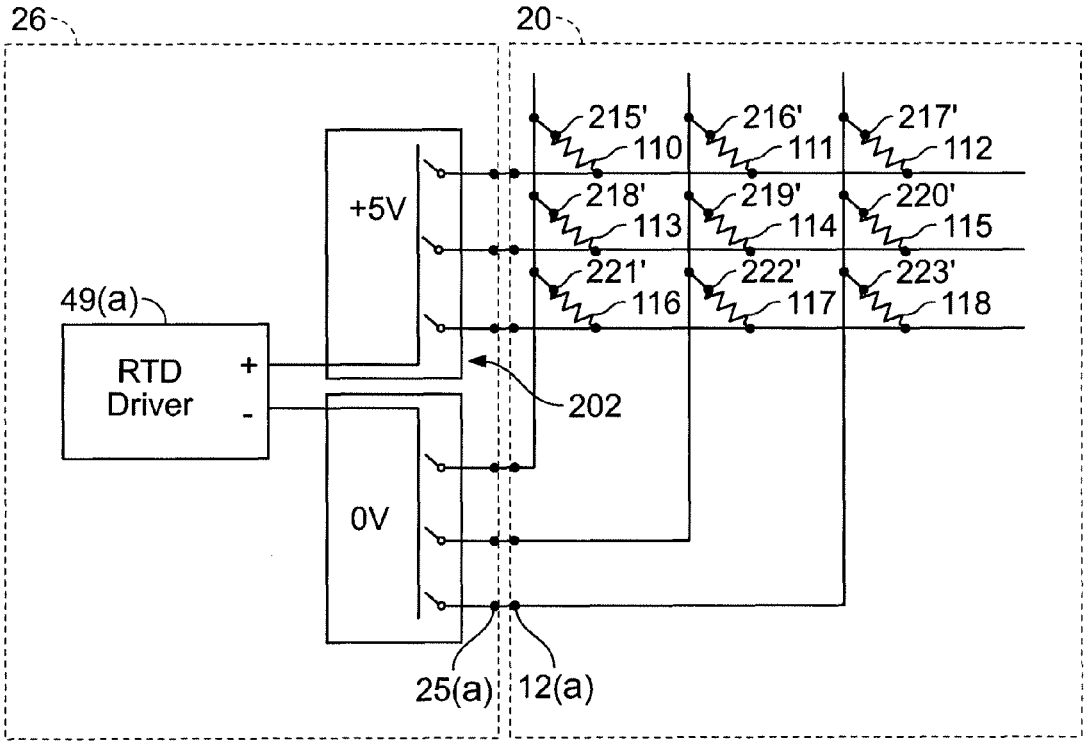
FIGS. 9A-B illustrate a technique for sharing conductive leads for combined heat source temperature sensors, which can be resistive temperature detectors ("RTDs")
Figure 9B:
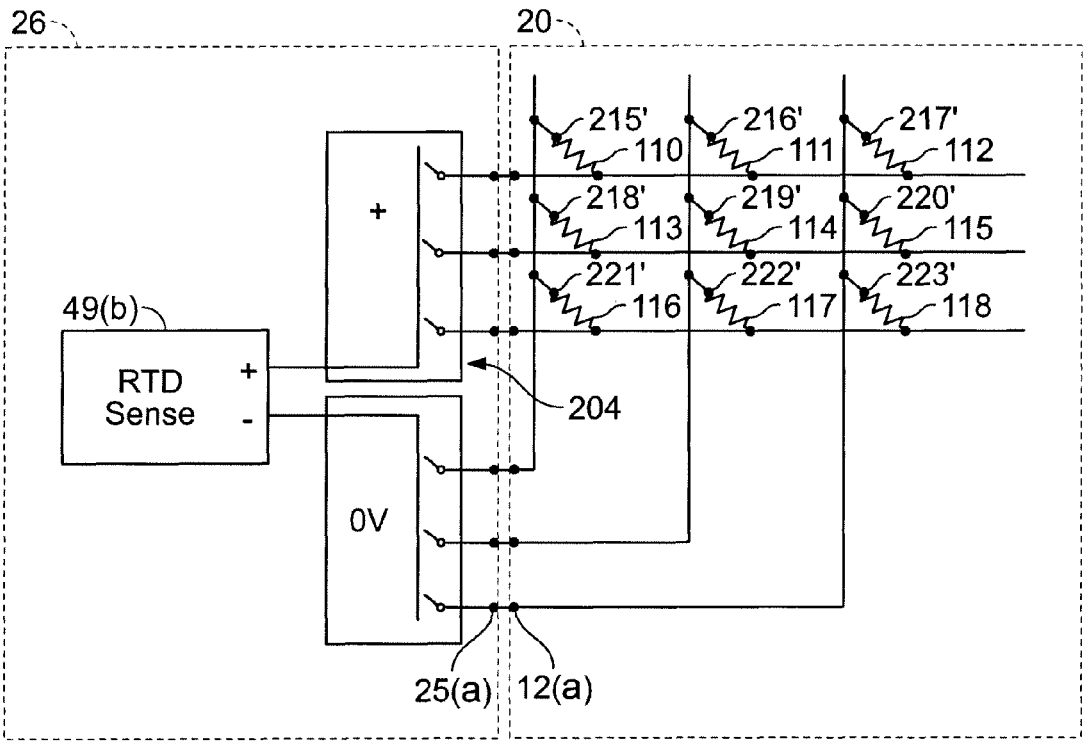

FIGS. 9A, 9B, 10A, 10B depict similar arrays for the resistive components used to sense temperature, such as R2 shown in FIG. 5. FIG. 9A depicts one array of leads for supplying current to sensing resistors 110-118. FIG. 9B depicts another set of leads for measuring the voltage across the same resistors. With this structure, the leads that are used to stimulate the "resistive sensors carry no current from the heat source driver 47 because they are electrically isolated from driver 47. Similarly, the leads for sensing the voltage of the resistive sensors 110-118 (FIG. 9B) carry essentially no current because they are isolated from the leads that supply current from drivers 47 and 49(a) (shown in FIGS. 8A, 8B and 9A).

Figure 10A:
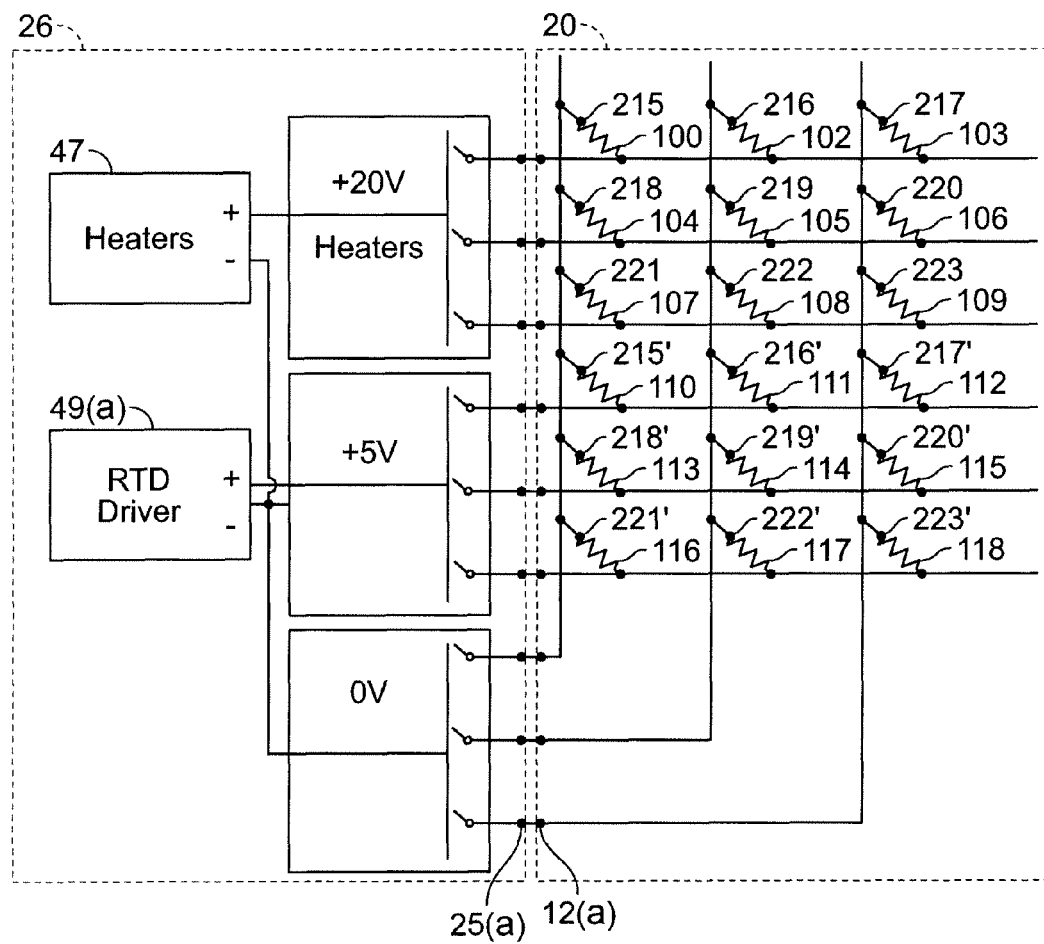
FIGS. 10A-B illustrate a technique for sharing conductive leads for combined heat source temperature sensors.
Figure 10B:
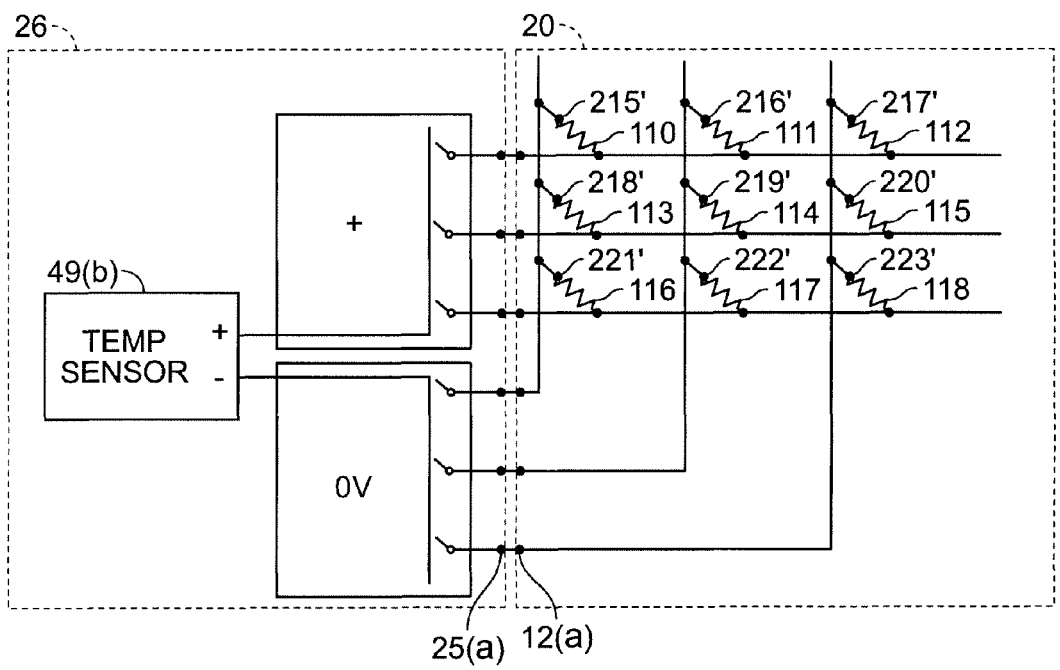

FIGS. 10A, 10B depict an alternative structure. As with the structure shown in FIGS. 9A, 9B, the leads for sensing the voltage across temperature sensing resistors, 110-118, are isolated from both of the current sources (heat source driver 47 and RTD driver 49(a)). However, both current sources 47, 49(a) share the same leads for current return, i.e., the leads depicted as columns in the array. This provides greater compression of the number of leads; however, the resistivity in the shared return leads may reduce the accuracy of the temperature measurement.

The arrays of FIGS. 9A, 9B, 10A, and 10B include current flow directional elements 215'-223', which allow current to flow in only one direction through sensing resistors 110-118.

Thus, current flow directional elements 215'-223' preferably allow current to flow in only one direction between the positive terminal of RTD drive or RTD sense and the negative or ground terminal of RID drive or RID sense along a current path that includes one of sensing resistors 110-118. Typically, current flow directional elements 215'-223' allow current to flow from the positive terminal to the negative terminal or ground terminal of either RTD drive or RTD sense but not from the negative or ground terminal to the positive terminal thereof. Current flow directional elements 215'-223' may be diodes similar to current flow directional elements 70, 71.

Components Having a Plurality of Heat Sources

One technique that typically reduces the number of contacts required to operate a plurality of heat sources is to integrate multiple heat sources into a single components.

Figure 11:
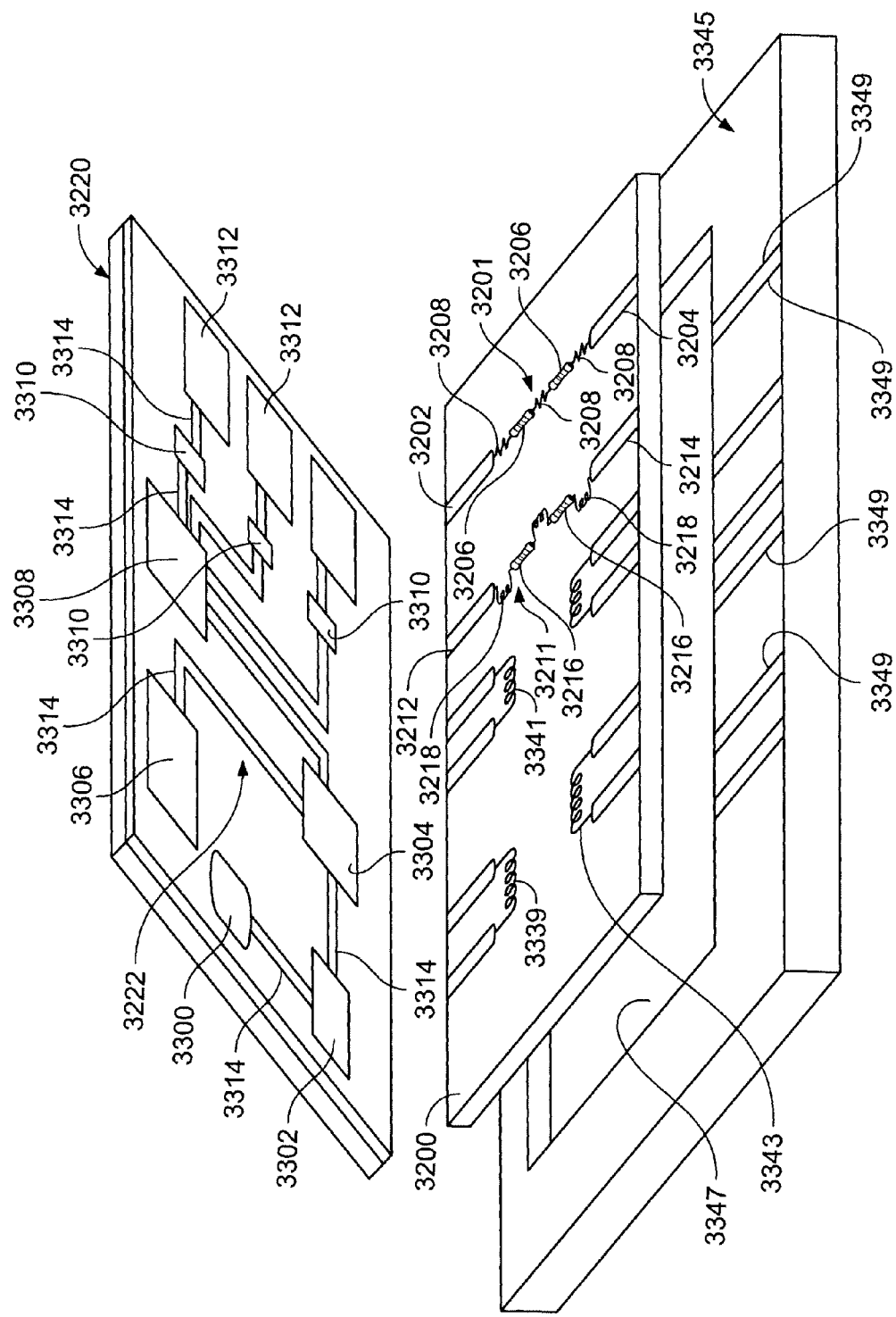
FIG. 11 is a portion of a microfluidic system having a microfluidic device defining a microfluidic network in thermal communication with heat sources of a substrate.

Referring to FIG. 11, a substrate 3200 includes a conductor 3201 defining a first end 3202 and a second end 3204. Between the first and second ends, conductor 3201 includes a plurality of connective regions 3206 having a first conductivity and a plurality of active regions 3208 having a second, lower conductivity. The various connective and active regions of conductor 3201 are connected in series, with consecutive active regions 3208 spaced apart by a connective region 3206. Conductor 3201 and consecutive connective regions 3206 thereof define a major longitudinal axis, which intersects at least a plurality of the regions 3206 and 3208.

Substrate 3200 typically has a lower electrical and thermal conductivity than conductor 3201, e.g., the substrate may be non-conductive. Substrate 3200 is typically fabricated from materials including, e.g., silicon, various oxides, organic compounds, quartz, glass, polymers, polyamide, polyimide, imide-triazine, glass-epoxy, and combinations thereof. In some embodiments, substrate 3200 is fabricated of materials typically used in printed circuit boards, e.g., a polyimide wafer. In some embodiments, the electrical leads supplying current to the heat sources are fabricated on the wafer so that there is no change in substrate between the interconnects to the power supplies and DAQ the heat sources. In some embodiments, substrate 3200 is fabricated of materials more flexible than quartz or silicon.

Typically, conductor 3201 is formed of metal deposited upon substrate 3200. For example, a metal foil about 2 mils thick can be bonded to the substrate and etched to prepare a pattern of heat sources and conductors. In some embodiments, some or all of conductor 3201 is sandwiched between layers of substrate 3200. For example, conductor 3201 may be covered by a non-conductive coating such as an oxide or polymer coating. In other embodiments, conductor 3201 is covered by a layer having an isotopic thermal conductivity. Typically, the thermal conductivity is highest normal to the surface of substrate 3200 and lower in the plane of the surface.

Active regions 3208 typically have a higher resistance than connective regions 3208. Thus, current flowing through conductor 3201 dissipates more heat within active regions 3208 than within connective regions 3206 so that each active region 3208 operates as a heat source. The amount of heat generated in different active regions may be different so that one active region dissipates more heat than another active region when current flows through conductor 3201. In some embodiments, the active regions have a smaller cross sectional area taken along a dimension generally perpendicular to a current pathway through the conductor.

Alternatively or in combination with varying the cross sectional area of the active and conductive regions, conductivity differences can be achieved by incorporating different materials within each type of region. In some embodiments, the active regions include a junction between dissimilar materials, e.g., different metals. Passage of current through the junction generates heat. In some embodiments, passage of current through the junction reduces the temperature of the junction and provides a cooling effect. In general, however, the active and connective regions are formed of the same material.

Substrate 3200 also includes a second conductor 3211 defining a first end 3212 and a second end 3214. Between the first and second ends, conductor 3211 includes a plurality of connective regions 3216 having a first conductivity and a plurality of active regions 3218 typically having a second, lower conductivity. The various connective and active regions of conductor 3211 are connected in series, with consecutive active regions 3218 spaced apart by a connective region 3216. Consecutive connective regions 3216 generally (but not necessarily) define a major longitudinal axis. At least some of the active regions 3218 are disposed laterally to the longitudinal axis of consecutive connective regions. In other respects, however, connective and active regions of conductor 3211 may be identical with connective and active regions of conductor 3201.

Substrate 3200 also includes heat sources 3339, 3341, and 3343, which are not multiplexed. Thus, passing current through these heat sources typically generates heat within a single locality of substrate 3200.

Substrate 3200 is received by (or is integral with) a chip carrier cartridge 3345, similar to chip carrier cartridge 20. Cartridge 3345 includes connections 3349 that allow electrical and other signals to be input to and received from substrate 3200. Connections 3349 are generally in communication with a DAQ configured to operate heat sources of substrate 3200. Cartridge 3345 is typically a PCB and can be configured to receive a plurality of different substrates 3200, each having a different pattern of heat sources configured to actuate components of a different microfluidic network.

In use, substrate 3200 mates with a microfluidic device 3220 comprising a plurality of layers defining a microfluidic network 3222 therebetween. Typically, device 3220 and substrate 3200 mate with a precision of better than 100 microns in dimensions parallel to the planes of the substrate and device.

Network 3222 includes an input module 3300, an enrichment module 3302, a lysing module 3304, an actuator 3306, a DNA clean-up module 3308, a plurality of fluid control elements 3310, and a plurality of reaction-detection chambers 3312. Various components of network 3222 are connected by channels 3314. Various microfluidic devices and fabrication techniques are discussed in The Processing Application.

When device 3220 is mated with substrate 3200, active regions 3208 and 3218 are disposed in thermal communication with thermally actuated elements of the microfluidic network. For example, active regions 3208 thermally communicate with reaction-detection modules 3312 and active regions 3218 thermally communicate with fluid control elements 3310.

Typically, heat sources (active regions) of substrate 3200 in thermal communication with valves and gates of device 3220 are configured to heat an area of device 3220 that is somewhat larger than the area occupied by TRS of the valves or gates.

Whether for a gate or a valve, the obstructing mass of TRS can have a volume of 250 nl or less, 125 nl or less, 75 nl or less, 50 nl or less, 25, nl or less, 10 nl or less, 2.5 nl or less, 1 nl or less, e.g., 750 pico liters or less. In some embodiments of a gate or valve, some or all of the TRS passes downstream upon opening the gate or valve. For example, the TRS may pass downstream along the same channel as sample previously obstructed by the TRS. In some embodiments, the TRS melts and coats walls of the channel downstream from the position occupied by the TRS in the closed state. The walls may be at least partially coated for several mm downstream. In some embodiments, the TRS disperses and passes downstream as particles too small to obstruct the channel.

Upon passing a current through conductor 3201, active regions 3208 typically dissipate an amount of heat proportional to the magnitude of the current and to the resistance of the active region. The heat raises the temperature of material with reaction-detection modules 3318. In some embodiments, a respective polymerase chain reaction mixture present in each module 3318 can be heated and allowed to cool repeatedly to allow amplification of DNA present therein. In some embodiments, device 3220 includes a plurality of lysing modules that mate with different active regions of a conductor. The active regions generate heat to lyse cells present in respective lysing modules. Reaction-detection and lysing modules are disclosed in The Processing Application.

Fluid control elements 3310 are valves or gates that selectively obstruct passage (in a closed state) or allow passage (in an open state) of material along channel 3314 between clean-up module 3308 and reaction-detection modules 3312. Passing current through conductor 3211 simultaneously actuates all of the elements 3310.

In some embodiments, the actuation simultaneously opens some valves and closes others. In other embodiments, all of the valves are simultaneously actuated from one state to another state.

Active regions of a single conductor can be actuated to, e.g., close multiple valves simultaneously, open multiple gates simultaneously, open multiple gates and close multiple valves simultaneously, heat multiple reaction chambers to simultaneously perform multiple reactions, e.g., isothermal reactions, thermocycling, simultaneously, or generate pressures and/or vacuums in multiple on-chip pumps simultaneously. In some embodiments, the thermally actuated elements associated with the active regions of conductor 3201 include a combination of components selected from the group including, e.g., valves, gates, reaction chambers, pressure sources, vacuum sources, and the like.

Conductive regions 3206 generally do not dissipate sufficient heat to actuate thermally actuated components of the device or cause evaporation of liquids within the microfluidic network. For example, the temperature generated within device 3220 may drop by 30° C. or more, by 50° C. or more, or by 75° or more between consecutive active regions. Consecutive active regions can be spaced apart by, e.g., 2 cm or less, 1 cm or less, or 5 mm or less.

In general, each active region heats only a localized region of a given microfluidic network so that the heat generated by an active region is sufficient to actuate only a single element of the microfluidic network.

Rather than having a single microfluidic network, a microfluidic device can include a plurality of separate microfluidic networks. Each network is configured to process a different sample and/or control. In some embodiments, different networks are configured to perform a different function, e.g., sample enrichment, cellular lysing, sample cleanup, detection, polynucleotide amplification, and the like. The different networks can be located within a single substrate.

Active regions connected in series, as are 3208 and 3218, typically pass an identical amount of current. Active regions can also be connected in parallel with one another. A first active region in parallel with a second active region generally passes an amount of current related to the magnitude of the current passing through the conductor and the ratio of the resistance of the first active region to the total resistance of the first and second active regions.

Figure 12A:
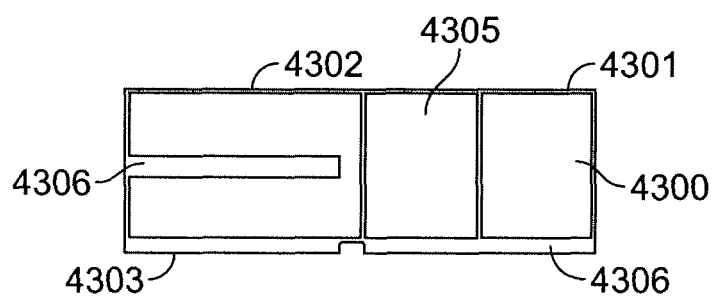
FIG. 12A is a side view of a substrate having a combined heat source temperature sensor and a conductive via for providing current to the combined heat source temperature sensor.
Figure 12B:
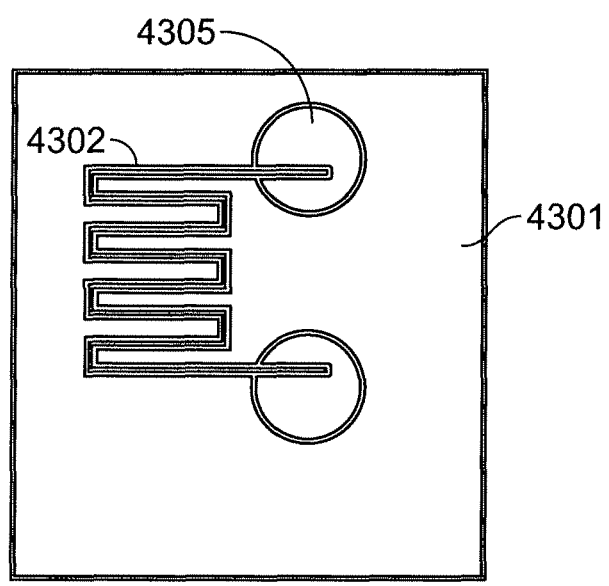
FIG. 12B is a top view of the substrate of FIG. 12A.

Exemplary techniques for fabricating substrates such as substrate 3200 are discussed with respect to FIGS. 12*a* and 12*b* in which an substrate 4300 defines a generally flat upper surface 4301 and a lower surface 4303. Upper surface 4301 includes a plurality of active regions 4302 (e.g., heat elements, temperature sensors, or combinations thereof) only one of which is shown.

Conductive vias 4305 typically pass partially or completely through substrate 4300 so that leads 4306 that supply current to active regions 4302 are spaced apart from an upper surface 4301 by at least a portion of substrate 4300. Thus, leads 4306 are generally buried in within substrate 4300 and/or run along lower surface 4303. Use of vias to provide active regions with current allows the density of active regions to be increased compared to fabricating both leads and active regions on the same surface of the substrate.

Methods for creating substrate 4300 include flip chip techniques. Generally, an organic substrate such as a PCB is cut into a desired shape, e.g., rectangular or circular. Flats to facilitate handling of the substrate in semiconductor processing equipment may be provided. Holes are formed to accommodate vias and the vias formed using standard circuit board techniques. Connective regions (leads) are applied, e.g., to the back side of the substrate, to provide electrical contact between the vias of different active regions. The connective regions are generally copper interconnects or wires having a minimal width of about 35 microns to 100 microns and a thickness of about 12.5 microns to about 35 microns.

The upper surface of the substrate is polished until smooth. In some embodiments, the surface roughness is reduced to less than about 15%, e.g., less than about 10% of the active regions to be applied. In some embodiments, the top surface is polished to create a smooth surface, e.g., a surface finish of SPI A1/SPI A2/SPI A3, such as for crack-free deposition and lithograph y of thin films.

Photoresist is applied to the upper surface of the substrate to obtain a resist film, e.g., a film thickness of about 1 micron. The substrate is baked at a temperature that will minimize or prevent warping of the substrate yet cure the resist. Generally, the substrate is soft-baked at a temperature of less than about 100° C., e.g., less than about 90° C.

The resist film is exposed, e.g., to UV light, through a mask to transfer a pattern of active regions onto the resist. The exposed resist is developed to remove undesired resist. A thin conductive layer, e.g., a layer having a thickness of typically less than a micron, e.g., from about 0.1 to about 1 microns in thickness, is applied to the upper layer. For a given surface area, thinner layers have a higher resistance and will create higher temperatures in a microfluidic device. The resist is removed leaving behind the patterned active regions. During processing, the backside of the PCB may be protected using a resist film.

Alternatively, metal film can be deposited over the entire upper surface of the substrate. Resist is applied to the metal film and exposed using and the resist developed. Unwanted metal film is removed leaving the patterned active regions.

After forming the pattern of active regions, the substrate is cleaned and a typically non-conductive barrier layer applied to protect the active regions and prevent unwanted electrical contact to the active regions. In general, the barrier is applied at temperatures of less than about 35° C.

Once the active regions have been patterned, contacts are applied to provide electrical communication between the active regions and data acquisition and control circuitry.

While the invention has been illustratively described herein with reference to certain aspects, features and embodiments, it will be appreciated that the utility and scope of the invention is not thus limited and that the invention may readily embrace other and differing variations, modifications and other embodiments. For example, the same techniques for reducing the number of leads may be-applied to other types of components, not just resistors. The invention therefore is intended to be broadly interpreted and construed, as comprehending all such variations, modifications and alternative embodiments, within the spirit and scope of the ensuing claims.

What is claimed is:

1. A method of using a microfluidic system, comprising:
providing a first device comprising a first substrate defining a microfluidic network comprising at least one of each of a thermally actuated valve and a thermally actuated reaction chamber;
operatively receiving the first device in a second device, the second device comprising a second substrate defining a plurality of heat sources, each heat source being in thermal communication with a respective one of the thermally actuated valve and the thermally actuated reaction chamber of the first device, wherein at least one of the heat sources is a combined heating and temperature sensing element; and
controlling each heat source of the plurality of heat sources independently.

2. The method of claim 1, further comprising heating a respective one of the thermally actuated valve and the thermally actuated reaction chamber with the combined heating and temperature sensing element.

3. The method of claim 1, further comprising sensing a temperature of a respective one of the thermally actuated valve and the thermally actuated reaction chamber with the combined heating and temperature sensing element.

4. The method of claim 1, further comprising controlling the at least one of each of the thermally actuated valve and the thermally actuated reaction chamber independently of others.

5. The method of claim 1, further comprising heating only a localized region of the microfluidic network so that the heat generated is sufficient to actuate only a single element of the microfluidic network.

6. The method of claim 1, wherein the second device has a substantially lower thermal conductivity than the plurality of heat sources.

7. The method of claim 1, further comprising controlling the heat sources with control circuitry.

8. The method of claim 1, further comprising receiving signals in the second substrate from a data acquisition and control board.

9. The method of claim 1, wherein the combined heating and temperature sensing element comprises a resistive temperature sensor.

10. The method of claim 1, further comprising thermopneumatically actuating the thermally actuated valve.

11. The method of claim 1, further comprising thermal cycling the reaction chamber to perform a polymerase chain reaction.

12. The method of claim 1, wherein the thermally actuated valve comprises a temperature responsive substance.

13. The method of claim 12, wherein the temperature responsive substance is wax.

14. A method of using a microfluidic system, comprising:
providing a first device comprising a first substrate defining a microfluidic network comprising at least one of each of a thermally actuated valve and a thermally actuated reaction chamber;
operatively receiving the first device in a second device, the second device comprising a second substrate defining a plurality of heat sources, each heat source being in thermal communication with a respective one of the thermally actuated valve and the thermally actuated reaction chamber of the first device, wherein at least one of the heat sources is a combined heating and temperature sensing element; and
heating a thermally responsive substance and moving the thermally responsive substance into a channel of the microfluidic network.

15. The method of claim 14, wherein the temperature responsive substance is wax.

16. The method of claim 14, further comprising thermal cycling the reaction chamber to perform a polymerase chain reaction.

17. A method of using a microfluidic system, comprising:
providing a first device comprising a first substrate defining a microfluidic network comprising at least one of each of a thermally actuated valve and a thermally actuated reaction chamber;
operatively receiving the first device in a second device, the second device comprising a second substrate defining a plurality of heat sources, each heat source being in thermal communication with a respective one of the thermally actuated valve and the thermally actuated reaction chamber of the first device, wherein at least one of the heat sources is a combined heating and temperature sensing element; and
generating an amount of heat from a first heat source of the plurality of heat sources to actuate a first thermally actuated component but insufficient to actuate a second thermally actuated component.

18. The method of Claim 17, further comprising controlling the microfluidic system by electrical signals or optical signals received from a data acquisition and control board.

19. The method of claim 17, further comprising controlling a heat source of the plurality of heat sources independently of another heat source of the plurality of heat sources.

20. The method of claim 17, further comprising thermal cycling the reaction chamber to perform a polymerase chain reaction.

21. A method of using a microfluidic s stem, comprising:
providing a first device comprising a first substrate defining a microfluidic network comprising at least one of each of a thermally actuated valve and a thermally actuated reaction chamber;
operatively receiving the first device in a second device, the second device comprising a second substrate defining a plurality of heat sources, each heat source being in thermal communication with a respective one of the thermally actuated valve and the thermally actuated reaction chamber of the first device, wherein at least one of the heat sources is a combined heating and temperature sensing element; and
actuating one of the plurality of heat sources such that current flows in essentially only one direction through the heat source.

22. The method of claim 21, further comprising substantially preventing current flow in a second, opposite direction through the heat source.

23. The method of claim 21, further comprising controlling the heat sources with control circuitry.

24. The method of claim 21, further comprising thermal cycling the reaction chamber to perform a polymerase chain reaction.

* * * * *